United States Patent
Zheng et al.

(10) Patent No.: US 10,774,370 B2
(45) Date of Patent: Sep. 15, 2020

(54) METHODS AND COMPOSITIONS FOR NUCLEIC ACID ANALYSIS

(71) Applicant: 10X Genomics, Inc., Pleasanton, CA (US)

(72) Inventors: Xinying Zheng, Mountain View, CA (US); Serge Saxonov, Oakland, CA (US); Michael Schnall-Levin, San Francisco, CA (US); Kevin Ness, Pleasanton, CA (US); Rajiv Bharadwaj, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 742 days.

(21) Appl. No.: 15/367,660

(22) Filed: Dec. 2, 2016

(65) Prior Publication Data
US 2017/0159109 A1 Jun. 8, 2017

Related U.S. Application Data

(60) Provisional application No. 62/263,532, filed on Dec. 4, 2015.

(51) Int. Cl.
*C12Q 1/68* (2018.01)
*C12Q 1/6809* (2018.01)
*C12Q 1/6806* (2018.01)
*C12Q 1/6834* (2018.01)
*C12Q 1/6869* (2018.01)

(52) U.S. Cl.
CPC ......... *C12Q 1/6809* (2013.01); *C12Q 1/6806* (2013.01); *C12Q 1/6834* (2013.01); *C12Q 1/6869* (2013.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Gerald |
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,709,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Thompson |
| 6,303,343 B1 | 10/2001 | Kopf-Sill |

(Continued)

FOREIGN PATENT DOCUMENTS

| | | |
|---|---|---|
| CN | 102292455 A | 12/2011 |
| CN | 103202812 A | 7/2013 |

(Continued)

OTHER PUBLICATIONS

Splinter et al.( Methods in enzymology. vol. 375. Academic Press, 2003. 493-507). (Year: 2003).*

(Continued)

*Primary Examiner* — Tracy Vivlemore
*Assistant Examiner* — Sahana S Kaup
(74) *Attorney, Agent, or Firm* — Morgan, Lewis & Bockius, LLP

(57) ABSTRACT

The present invention is directed to methods, compositions and systems for analyzing sequence information while retaining structural and molecular context of that sequence information.

31 Claims, 7 Drawing Sheets

(56) References Cited

U.S. PATENT DOCUMENTS

| | | |
|---|---|---|
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Stone et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,137,449 B2 | 11/2018 | Bharadwaj et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |

(56) References Cited

U.S. PATENT DOCUMENTS

| | | |
|---|---|---|
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101680 A1 | 5/2004 | Barber |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0187705 A1 | 7/2010 | Lee et al. |
| 2010/0210479 A1 | 8/2010 | Griffiths et al. |

(56) References Cited

U.S. PATENT DOCUMENTS

| | | |
|---|---|---|
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0287947 A1* | 11/2011 | Chen .................. G01N 33/5308 506/7 |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Zaag et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0295819 A1 | 11/2012 | Leamon et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0183672 A1* | 7/2013 | de Laat ................ C12Q 1/6855 435/6.11 |
| 2013/0189700 A1 | 7/2013 | So et al. |
| 2013/0203605 A1 | 8/2013 | Shendure et al. |
| 2013/0203675 A1 | 8/2013 | DeSimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0025726 A1 | 1/2016 | Altin et al. |

(56) References Cited

U.S. PATENT DOCUMENTS

| | | |
|---|---|---|
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0030515 A1 | 2/2018 | Regev et al. |
| 2018/0057868 A1 | 3/2018 | Walder et al. |
| 2018/0087050 A1 | 3/2018 | Zheng et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195112 A1 | 7/2018 | Lebofsky et al. |
| 2018/0216162 A1 | 8/2018 | Belhocine et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0274027 A1 | 9/2018 | Hindson et al. |
| 2018/0282804 A1 | 10/2018 | Hindson et al. |
| 2018/0327839 A1 | 11/2018 | Hindson et al. |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| EP | 2635679 B1 | 4/2017 |
| GB | 2097692 B | 5/1985 |
| GB | 2485850 A | 5/2012 |
| JP | 5949832 A | 3/1984 |
| JP | S60227826 A | 11/1985 |
| JP | 2006-507921 A | 3/2006 |
| JP | 2006-289250 A | 10/2006 |
| JP | 2007015990 A | 1/2007 |
| JP | 2007-268350 A | 10/2007 |
| JP | 2009513948 A | 4/2009 |
| JP | 2009-208074 | 9/2009 |
| JP | 2012131798 A | 7/2012 |
| WO | 1984002000 A1 | 5/1984 |
| WO | 1993001498 A1 | 1/1993 |
| WO | 1994018218 A1 | 8/1994 |
| WO | 1994019101 A1 | 9/1994 |
| WO | 1994023699 A1 | 10/1994 |
| WO | WO-1995030782 A1 | 11/1995 |
| WO | WO-1996029629 A2 | 9/1996 |
| WO | WO-1996041011 A1 | 12/1996 |
| WO | 1998002237 A1 | 1/1998 |
| WO | 1998052691 A1 | 11/1998 |
| WO | WO-1999009217 A1 | 2/1999 |
| WO | 1999042597 A1 | 8/1999 |
| WO | WO-1999052708 A1 | 10/1999 |
| WO | WO-2000008212 A1 | 2/2000 |
| WO | 2000023181 A1 | 4/2000 |
| WO | WO-2000026412 A1 | 5/2000 |
| WO | 2000043766 A1 | 7/2000 |
| WO | WO-2000070095 A2 | 11/2000 |
| WO | 2001002850 A1 | 1/2001 |
| WO | WO-2001014589 A2 | 3/2001 |
| WO | 2001090418 A1 | 11/2001 |
| WO | WO-2001089787 A2 | 11/2001 |
| WO | 2001027610 A3 | 3/2002 |
| WO | WO-2002031203 A2 | 4/2002 |
| WO | WO-2002086148 A1 | 10/2002 |
| WO | 2002018949 A3 | 1/2003 |
| WO | 2003062462 A2 | 7/2003 |
| WO | WO-2004002627 A2 | 1/2004 |
| WO | WO-2004010106 A2 | 1/2004 |
| WO | 2004061083 A2 | 7/2004 |
| WO | 2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | 2007012638 A1 | 2/2007 |
| WO | 2007018601 A1 | 2/2007 |
| WO | WO-2007024840 A2 | 3/2007 |
| WO | 2007084192 A2 | 7/2007 |
| WO | WO-2007081385 A2 | 7/2007 |
| WO | WO-2007081387 A1 | 7/2007 |
| WO | 2007093819 A2 | 8/2007 |
| WO | WO-2007089541 A2 | 8/2007 |
| WO | 2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | 2007147079 A2 | 12/2007 |
| WO | WO-2007138178 A2 | 12/2007 |
| WO | WO-2007139766 A2 | 12/2007 |
| WO | WO-2007140015 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | 2008061193 A3 | 11/2008 |

(56) References Cited

FOREIGN PATENT DOCUMENTS

| | | |
|---|---|---|
| WO | WO-2008134153 A1 | 11/2008 |
| WO | 2008150432 A1 | 12/2008 |
| WO | 2009015296 A1 | 1/2009 |
| WO | WO-2009005680 A1 | 1/2009 |
| WO | WO-2009011808 A1 | 1/2009 |
| WO | 2009048532 A2 | 4/2009 |
| WO | WO-2009061372 A1 | 5/2009 |
| WO | WO-2009085215 A1 | 7/2009 |
| WO | 2009147386 A1 | 12/2009 |
| WO | 2010009735 A2 | 1/2010 |
| WO | WO-2010004018 A2 | 1/2010 |
| WO | WO-2010033200 A2 | 3/2010 |
| WO | 2010048605 A1 | 4/2010 |
| WO | 2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | 2010117620 A3 | 2/2011 |
| WO | 2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | 2011140627 A1 | 11/2011 |
| WO | WO-2012012037 A1 | 1/2012 |
| WO | 2012047889 A2 | 4/2012 |
| WO | 2012048340 A2 | 4/2012 |
| WO | WO-2012048341 A1 | 4/2012 |
| WO | 2012061832 A1 | 5/2012 |
| WO | 2012112804 A1 | 8/2012 |
| WO | WO-2012106546 A2 | 8/2012 |
| WO | WO-2012112970 A2 | 8/2012 |
| WO | WO-2012083225 A2 | 9/2012 |
| WO | 2012136734 A1 | 10/2012 |
| WO | 2012140224 A1 | 10/2012 |
| WO | WO-2012142611 A2 | 10/2012 |
| WO | 2012148497 A2 | 11/2012 |
| WO | WO 2012/150317 A1 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | 2013055955 A1 | 4/2013 |
| WO | 2013096643 A1 | 6/2013 |
| WO | WO-2013122996 A1 | 8/2013 |
| WO | WO-2013123125 A1 | 8/2013 |
| WO | WO 2013126741 A1 | 8/2013 |
| WO | WO 2013134261 A1 | 9/2013 |
| WO | WO 2013150083 A1 | 10/2013 |
| WO | WO-2013177220 A1 | 11/2013 |
| WO | 2013188872 A1 | 12/2013 |
| WO | WO-2014028537 A1 | 2/2014 |
| WO | 2014053854 A1 | 4/2014 |
| WO | 2014071361 A1 | 5/2014 |
| WO | WO-2014074611 A1 | 5/2014 |
| WO | WO-2014093676 A1 | 6/2014 |
| WO | 2014108810 A2 | 7/2014 |
| WO | 2014140309 A1 | 9/2014 |
| WO | 2014144495 A1 | 9/2014 |
| WO | 2014145047 A1 | 9/2014 |
| WO | 2014150931 A1 | 9/2014 |
| WO | 2014182835 A1 | 11/2014 |
| WO | 2014189957 A2 | 11/2014 |
| WO | 2014200767 A1 | 12/2014 |
| WO | WO-2014210353 A2 | 12/2014 |
| WO | 2015031691 A1 | 3/2015 |
| WO | WO-2015044428 A1 | 4/2015 |
| WO | WO-2015089243 A1 * | 6/2015 | ............ C12Q 1/6844 |
| WO | WO-2015123588 A1 * | 8/2015 | ............ C12Q 1/6809 |
| WO | WO-2015164212 A1 | 10/2015 |
| WO | 2015185067 A1 | 12/2015 |
| WO | 2015188839 A2 | 12/2015 |
| WO | 2016040476 A1 | 3/2016 |
| WO | 2016061517 A2 | 4/2016 |
| WO | 2016126871 A2 | 8/2016 |
| WO | 2016162309 A1 | 10/2016 |
| WO | 2016166128 A1 | 10/2016 |
| WO | 2016187717 A1 | 12/2016 |
| WO | 2016191618 A1 | 12/2016 |
| WO | 2016207647 A1 | 12/2016 |
| WO | 2016207653 A1 | 12/2016 |
| WO | 2016207661 A1 | 12/2016 |
| WO | 2017015075 A1 | 1/2017 |
| WO | 2017025594 A1 | 2/2017 |
| WO | 2017053905 A1 | 3/2017 |
| WO | 2017075265 A1 | 5/2017 |
| WO | 2017075294 A1 | 5/2017 |
| WO | 2017156336 A1 | 9/2017 |
| WO | 2018045186 A1 | 3/2018 |
| WO | 2018119447 A2 | 6/2018 |

OTHER PUBLICATIONS

Gao et al.[abstract]. In: Proceedings of the 106th Annual Meeting of the American Association for Cancer Research; Apr. 18-22, 2015; Philadelphia, PA. Philadelphia (PA): AACR; Cancer Res 2015;75(15 Suppl) (Year: 2015).*

EPO Examination Report dated Mar. 6, 2019 for EP Application No. 16822294.1, 5 pages.

P. Cejas et al.: "Chromatin immunoprecipitation from fixed clinical tissues reveals tumor-specific enhancer profiles", Nature Medicine, vol. 22, No. 6, Apr. 25, 2016, pp. 685-691.

M. Fanelli et al.: "Pathology tissue-chromatin immunoprecipitation, coupled with high-throughput sequencing, allows the epigenetic profiling of patient samples", Proceedings of the National Academy of Sciences of the United States of America, vol. 107, No. 50, Nov. 24, 2010, pp. 21535-21540.

M. Mignardi et al.: "Oligonucleotide gap-fill ligation for mutation detection and sequencing in situ", Nucleic Acids Research, vol. 43, No. 22, Dec. 15, 2015, pp. e151-e151.

Abate et al., Valve-based flow focusing for drop formation. Appl Phys Lett. 2009;94. 3 pages.

Abate, A.R. et al. "Beating Poisson encapsulation statistics using close-packed ordering" Lab on a Chip (Sep. 21, 2009) 9(18):2628-2631.

Abate, et al. High-throughput injection with microfluidics using picoinjectors. Proc Natl Acad Sci U S A. Nov. 9, 2010;107(45):19163-6. doi: 10.1073-pNas.1006888107. Epub Oct. 20, 2010.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

Aitman, et al. Copy number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Biol., 329:196-205 (2006).

Akselband, "Rapid mycobacteria drug susceptibility testing using gel microdrop (GMD) growth assay and flow cytometry", J. Microbiol. Methods, 62:181-197 (2005).

Altemos et al., "Genomic Characterization of Large Heterochromatic Gaps in the Human Genome Assembly," PLOS Computational Biology, May 15, 2014, vol. 10, Issue 5, 14 pages.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al., "Formation of dispersions using 'flow focusing' in microchannels", Appln. Phys. Letts. 82:3 364 (2003).

Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.

Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.

(56) References Cited

OTHER PUBLICATIONS

Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, U.M et al., "Micro-injection moulding of polymer microfluidic devices" Microfluidics and nanofluidics (2009) 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016-j.ajhg.2007.08. 001.
Baret et al. "Fluorescence-activated droplet sorting (FADS): efficient microfluidic cell sorting based on enzymatic activity" Lab on a Chip (2009) 9(13):1850-1858.
Berkum et al., "Hi-C: A Method to Study the Three-dimensional Architecture of Genomes," J Vis Exp (39), e1896, doi:10.3791/1869 (2010).
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039-b814810d. Epub Nov. 20, 2008.
Brouzes, E et al., "Droplet microfluidic technology for single-cell high-throughput screening" PNAS (2009) 106(34):14195-14200.
Browning, S.R. et al. "Haplotype Phasing: Existing Methods and New Developments" NaRevGenet (Sep. 16, 2011) 12(10):703-714.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in *Escherichia coli* as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, F et al., "Chemical transfection of cells in picoliter aqueous droplets in fluorocarbon oil" Anal. Chem. (2011) 83:8816-8820.
Choi et al. "Identification of novel isoforms of the EML4-ALK transforming gene in non-small cell lung cancer," Cancer Res (2008) 68:4971-4976.
Chokkalingam, V et al., "Probing cellular heterogeneity in cytokine-secreting immune cells using droplet-based microfluidics" Lab Chip (2013) 13:4740-4744.
Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.
Chu, L-Y. et al., "Controllable monodisperse multiple emulsions" Angew. Chem. Int. Ed. (2007) 46:8970-8974.
Chung et al., "Structural and molecular interrogation of intact biological systems," Nature, May 16, 2013, 23 pages.
Clausell-Tormos et al., "Droplet-based microfluidic platforms for the encapsulation and screening of mammalian cells and multicellular organisms", Chem. Biol. 15:427-437 (2008).
Cook, et al. Copy-number variations associated with neuropsychiatric conditions. Nature. Oct. 16, 2008;455(7215):919-23. doi: 10.1038-nature07458.
Coufal, et al. L1 retrotransposition in human neural progenitor cells. Nature. Aug. 27, 2009;460(7259):1127-31. doi: 10.1038/nature08248. Epub Aug. 5, 2009.
De Bruin et al., UBS Investment Research. Q-Seriesï¿½: DNa Sequencing. UBS Securities LLC. Jul. 12, 2007. 15 pages.
Dekker et al., "Capturing chromosome conformation," Science 295:1306-1311 (2002).
Demirci, et al. "Single cell epitaxy by acoustic picolitre droplets" Lab Chip. Sep. 2007;7(9):1139-45. Epub Jul. 10, 2007.
Doerr, "The smallest bioreactor", Nature Methods, 2:5 326 (2005).
Doshi, N. et al. "Red blood cell-mimicking synthetic biomaterial particles" PNAS (2009) 106(51):21495-21499.
Dowding, et al. "Oil core-polymer shell microcapsules by interNal phase separation from emulsion droplets. II: controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Dressman et al. "Transforming single DNA molecules into fluorescent magnetic particles for detection and enumeration of genetic variations" PNAS (2003) 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, D.J. et al., "Ultrahigh-throughput mammalian single-cell reverse-transcriptase polymerase chain reaction in microfluidic droplets" Anal. Chem. (2013) 85:8016-8021.
Esser-Kahn, et al. Triggered release from polymer capsules. Macromolecules. 2011; 44:5539-5553.
Fabi, et al. Correlation of efficacy between EGFR gene copy number and lapatinib-capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, S. et al. "A Scalable, fully automated process for construction of sequence-ready human exome targeted capture libraries" Genome Biology (2011) 2:R1-R15. doi: 10.1186-gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10. 1038/nbr.2696.
Fredrickson, C.K. et al., "Macro-to-micro interfaces for microfluidic devices" Lab Chip (2004) 4:526-533.
Freiberg, et al. "Polymer microspheres for controlled drug release" Int J Pharm. Sep. 10, 2004;282(1-2):1-18.
Fu. A.Y. et al. "A microfabricated fluorescence-activated cell sorter" Nature Biotech (Nov. 1999) 17:1109-1111.
Fulton et al., "Advanced multiplexed analysis with the FlowMetrix system" Clin Chern. Sep. 1997;43(9): 1749-56.
Garstecki, P. et al. "Formation of monodisperse bubbles in a microfluidic flow-focusing device" Appl. Phys. Lett (2004) 85(13):2659-2651. DOI: 10.1063-1.1796526.
Gartner, et al. The Microfluidic Toolbox ï¿½ examples for fluidic interfaces and standardization concepts. Proc. SPIE 4982, Microfluidics, BioMEMS, and Medical Microsystems, (Jan. 17, 2003); doi: 10.1117-12.479566.
Gericke, M. et al. "Functional Cellulose Beads: Preparation, Characterization, and Applications" Chem Rev (2013) 113(7):4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1-AIDS susceptibility. Science. Mar. 4, 2005;307(5714):1434-40. Epub Jan. 6, 2005.

(56) References Cited

OTHER PUBLICATIONS

Granieri, Lucia "Droplet-based microfluidics and engineering of tissue plasminogen activator for biomedical applications" Ph.D. Thesis, Nov. 13, 2009 (131 pages).
Grasland-Mongrain, E. et al. "Droplet coalescence in microlfuidic devices" Internet Citation, 2003, XP002436104, Retrieved from the Internet: URL:http:--www.eleves.ens.fr.-home-grasland-rapports-stage4.pdf [retrieved on Jun. 4, 2007].
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T et al. "CEL-Seq: Single-Cell RNa-Seq by Multiplexed Linear Amplification" Cell Rep. Sep. 27, 2012;2(3):666-73. doi: 10.1016-j.celrep.2012.08.003. Epub Aug. 30, 2012.
He, M. et al. "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hjerten, S. et al. "General methods to render mcaroporous stationary phases nonporous and deformable, exemplified with agarose and silica beads and their use in high-performance ion-exchange and hydrophobic-interaction chromatography of proteins" Chromatographia (Jan. 1991) 31(1-2):85-94.
Holtze, C. et al. Biocompatible surfactants for water-in-fluorocarbon emulsions. Lab Chip. Oct. 2008;8(10):1632-9. doi: 10.1039-b806706f. Epub Sep. 2, 2008.
Huebner, "Quantitative detection of protein expression in single cells using droplet microfluidics", Chem. Commun. 1218-1220 (2007).
Hug, H. et al. "Measurement of the number of molecules of a single mRNA species in a complex mRNA preparation" J Theor Biol. Apr. 21, 2003;221(4):615-24.
Ioannidis, N "Manufacturing of agarose-based chromatographic media with controlled pore and particle size" (2009) XP055289233, Retrieved from the Internet: URL: http://etheses.bham.ac.uk/368/3/Ioannidis09PhD.pdf.
Illumina TrueSeq Custom Enrichment Kit, pp. 1-4 (2011-2012).
Jena et al., "Cyclic olefin copolymer based microfluidic devices for biochip applications: Ultraviolet surface grafting using 2-methacryloyloxyethyl phosphorylcholine" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Kaper et al., PNAS, vol. 110, pp. 5552-5557 (Apr. 2013).
Kaper et al., Pnas, vol. 110, (Apr. 2013) Supplemental date pp. 1-7.
Karamkar et al., "Organocatalytic removal of formaldehyde adducts from RNA and DNA bases," Nature Chemistry, 2015, doi:10.1038/nchm.2307.
Kebschull et al., "High-Throughput Mapping of Single-Neuron Projections by Sequencing of Barcoded RNA," Neuron, vol. 91, Issue 5, Sep. 7, 2016, p. 975-987.
Khomiakov A et al., "Analysis of perfect and mismatched DNA duplexes by a generic hexanucleotide microchip". Mol Biol (Mosk). Jul.-Aug. 2003;37(4):726-41. Russian. Abstract only.
Kim, et al. Albumin loaded microsphere of amphiphilic poly(ethylene glycol)-poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Kim, J et al., "Rapid prototyping of microfluidic systems using a PDMS-polymer tape composite" Lab Chip (2009) 9:1290-1293.
Kitzman, et al. Noninvasive whole-genome sequencing of a human fetus. Sci Transl Med. Jun. 6, 2012;4(137):137ra76. doi: 10.1126-scitranslmed.3004323.

Klein, et al. Droplet barcoding for single-cell transcriptomics applied to embryonic stem cells. Cell. May 21, 2015; 161:1187-1201.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip The Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Lee, J-H. et al. "Fluorescent in situ sequencing (FISSEQ) of RNA for gene expression profiling in intact cells and tissues" Nature Protocols (Feb. 12, 2015) 10(3):442-458.
Lee et al., "ACT-PRESTO: Rapid and consistent tissue clearing and labeling method for 3-dimensional (3D) imaging," Sci Rep., Jan. 11, 2016 doi: 10.1038/srep18631.
Li, Y., et al., "PEGylated PLGA Nanoparticles as protein carriers: synthesis, preparation and biodistribution in rats," Journal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro-Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6):703-707 (Jun. 2006).
Lowe, Adam J."Norbornenes and [n]polynorbornanes as molecular scaffolds for anion recognition" Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016-j.cell.2015.05.002.
Mair, D.A. et al., "Injection molded microfluidic chips featuring integrated interconnects" Lab Chip (2006) 6:1346-1354.
Makino, K. et al. "Preparation of hydrogel microcapsules Effects of preparation conditions upon membrane properties" Colloids and Surfaces: B Biointerfaces (1998) 12:97-104.
Marcus. Gene method offers diagnostic hope. The Wall Street Journal. Jul. 11, 2012.
Matochko, W.L. et al., "Uniform amplification of phage display libraries in monodisperse emulsions," Methods (2012) 58:18-27.
Mazutis, et al. Selective droplet coalescence using microfluidic systems. Lab Chip. Apr. 24, 2012;12(10):1800-6. doi: 10.1039-c2lc40121e. Epub Mar. 27, 2012.
Merriman, et al. Progress in ion torrent semiconductor chip based sequencing. Electrophoresis. Dec. 2012;33(23):3397-3417. doi: 10.1002-elps.201200424.
Microfluidic ChipShop. Microfluidic product catalogue. Mar. 2005.
Microfluidic ChipShop. Microfluidic product catalogue. Oct. 2009.
Mirzabekov, "DNA Sequencing by Hybridization—a Megasequencing Method and a Diagnostic Tool?" Trends in Biotechnology 12(1): 27-32 (1994).
Moore, J.L. et al., "Behavior of capillary valves in centrifugal microfluidic devices prepared by three-dimensional printing" Microfluid Nanofluid (2011) 10:877-888.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.

(56) References Cited

OTHER PUBLICATIONS

Muotri, et al. L1 retrotransposition in neurons is modulated by MeCP2. Nature. Nov. 18, 2010;468(7322):443-6. doi: 10.1038/nature09544.
Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.
Navin, N.E. "The first five years of single-cell cancer genomics and beyond" Genome Res. (2015) 25:1499-1507.
Nextera Enrichment Sample Preparation Guide from Illumina, pp. 1-69 (Feb. 2013).
Nguyen, et al. In situ hybridization to chromosomes stabilized in gel microdrops. Cytometry. 1995; 21:111-119.
Novak, R. et al., "Single cell multiplex gene detection and sequencing using microfluidicallygenerated agarose emulsions" Angew. Chem. Int. Ed. Engl. (2011) 50(2):390-395.
Oberholzer, et al. Polymerase chain reaction in liposomes. Chem Biol. Oct. 1995;2(10):677-82.
Ogawa, et al. Production and characterization of O—W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Oligotex Handbook. For purification of poly A+ RNA from total RNA and directly from cultured cells or tissues as well as purification of polyadenylated in vitro transcripts. Jun. 2012.
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.
Pinto, et al. Functional impact of global rare copy number variation in autism spectrum disorders. Nature. Jul. 15, 2010;466(7304):368-72. doi: 10.1038-nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Richardson, T.T. et al. "Novel inhibition of archaeal family-D DNA polymerase by uracil" Nucl Acids Res (2013) 41(7):4207-4218
Rogozin, I.B. et al. "A highly conserved family of inactivated archaeal B family DNA polymerases" Biology Direct (2008) 3:32-36.
Rogozin, I.B. et al. "A highly conserved family of inactivated archaeal B family DNA polymerases" Biology Direct (2008) 3:32-36.
Ropers. New perspectives for the elucidation of genetic disorders. Am J Hum Genet. Aug. 2007;81(2):199-207. Epub Jun. 29, 2007.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.

Schirinzi et al., Combinatorial sequencing-by-hybridization: analysis of the NFI gene. Genet Test. 2006 Spring;10(1):8-17.
Schmieder, R. et al. "Fast Identification and Removal of Sequence Contamination from Genomic and Metagenomic Datasets" PLoS ONE, (Mar. 9, 2011) 6(3):1-11.
Schmitt, "Bead-based multiplex genotyping of human papillomaviruses", J. Clinical Microbiol., 44:2 504-512 (2006).
Sebat, et al. Strong association of de novo copy number mutations with autism. Science. Apr. 20, 2007;316(5823):445-9. Epub Mar. 15, 2007.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shimkus et al. "A chemically cleavable biotinylated nucleotide: Usefulness in the recovery of protein-DNA complexes from avidin affinity columns" PNAS (1985) 82:2593-2597.
Shlien, et al. Copy number variations and cancer. Genome Med. Jun. 16, 2009;1(6):62. doi: 10.1186-gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073-pnas.0802970105. Epub Aug. 6, 2008.
Shuttleworth, et al. "Recognition of the pro-mutagenic base uracil by family B DNA polymerases from archaea" J Mol Biol (Mar. 26, 2004) 337(3):621-634.
Sigma, Streptavidin-agarose (S1638) product information sheet, (2007) www.sigma-aldrich.com.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki et al., "Whole-Brain Imaging with Single-Cell Resolution Using Chemical Cocktails and Computational Analysis," Cell, vol. 157, Issue 3, pp. 726-739 Apr. 24, 2014.
Tawfik, D.S. et al. "Man-made cell-like compartments for molecular evolution" Nature Biotech (Jul. 1998) 16:652-656.
Tayyab, S. et al. "Size exclusion chromatography and size exclusion HPLC of proteins" Biochem Ed, Pergamon, (1991) 19(3):149-152.
Tewhey, R. et al., "Microdroplet-based PCR enrichment for large-scale targeted sequencing" Nature Biotech. (2009) 27(11):1025-1031 and Online Methods (11 pages).
Theberge, A.B, et al. Microdropelts in microfluidics: an evolving platform for discoveries in chemsitry and biology. Angew Chem Int Ed Engl. Aug. 9, 2010;49(34):5846-68. doi: 10.1002-anie.200906653.
Tomer et al., "Advanced CLARITY for rapid and high-resolution imaging of intact tissues," Nature Protocols 9, p. 1682-1697 (2014) doi:10.1038/nprot.2014.123.
Tonelli, C. et al., "Perfluoropolyether functional oligomers: unusual reactivity in organic chemistry" J. Fluorine Chem. (2002) 118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093-protein-gzq032. Epub May 31, 2010.
Turner, et al. "Methods for genomic partitioning" Annu Rev Genomics Human Genet. (2009) 10:263-284. doi: 10.1146-annurev-genom-082908-150112. Review.

(56) References Cited

OTHER PUBLICATIONS

Wagner, O et al., "Biocompatible fluorinated polyglycerols for droplet microfluidics as an alternative to PEG-based copolymer surfactants" Lab Chip DOI:10.1039-C5LC00823A. 2015.
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Weaver, J.C. et al. "Rapid clonal growth measurements at the single-cell level: gel microdroplets and flow cytometry", Biotechnology, 9:873-877 (1991).
Wesolowska et al., "Cost-effective multiplexing before capture allows screening 25 000 clinically relevant SNPs in childhood acute lymphoblastic leukemia," Leukemia, vol. 25, pp. 1001-1006 (2001).
Whitesides, "Soft lithography in biology and biochemistry", Annual Review of Biomedical Engineering, 3:335-373 (2001).
Williams, R. et al. "Amplification of complex gene libraries by emulsion PCR" Nature Methods (Jul. 2006) 3(7):545-550.
Woo, et al. G-C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)-EDTA-base artificial restriction DNa cutter for versatile manipulation of doulbe-stranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021-bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zheng, X.Y. et al. "Haplotyping germline and cancer genomes with high-throughput linked-read sequencing" Nature Biotech (Feb. 1, 2016) 34(3):303-311.
Zhu, S. et al., "Synthesis and self-assembly of highly incompatible polybutadienepoly(hexafluoropropoylene oxide) diblock copolymers" J. Polym. Sci. (2005) 43:3685-3694.
Zimmermann et at., Microscale production of hybridomas by hypoosmolar electrofusion. Human Antibodies Hybridomas. Jan. 1992;3(1): 14-8.
Zong, C. et al. "Genome-wide detection of single-nucleotide and copy-number variations of a single human cell" Science. Dec. 21, 2012;338(6114):1622-6. doi: 10.1126-science.1229164.
Dressman et al. Supplementary Information pp. 1-2 of article published 2003, PNAS 100(15:8817-22).
Hamilton, A.J. "microRNA in erythrocytes" Biochem. Soc. Trans. (2010) 38, 229-231.
Han, X. et al. "CRISPR-Cas9 delivery to hard-to-transfect cells via membrane deformation" Science Advances (2015) 1(7): E1500454 (8 pages).
Hiatt, et al, "Parallel, tag-directed assembly of locally derived short sequence reads", Nat Methods., 7:119-122, 2010.
Hirsch et al. "Easily reversible desthiobiotin binding to streptavidin, avidin, and other biotin-binding proteins: uses for protein labeling, detection, and isolation" Analytical Biochem (2002) 308(2):343-357.
Hosokawa, M. et al. "Massively parallel whole genome amplification for single-cell sequencing using droplet microfluidics" Scientific Reports (2017) 7:5199 (11 pages).
Hosono, S. et al. "Unbiased whole-genomeamplification directly from clinical samples" Genome Res. May 2003; 13(5):954-64. Epub Apr. 14, 2003.
Imburgio, et al, "Studies of promoter recognition and start site selection by T7 RNA polymerase using a comprehensive collection of promoter variants", Biochemistry., 39:10419-30, 2000.
Kamperman, T. et al. "Centering Single Cells in Microgels via Delayed Crosslinking Supports Long-Term 3D Culture by Preventing Cell Escape" Small. Jun. 2017;13(22). doi: 10.1002/smll.201603711. Epub Apr. 28, 2017.
Katsura, S. et al. "Indirect micromanipulation of single molecules in water-in-oil emulsion" Electrophoresis (2001) 22(2):289-293.
Kenis, P.J. et al. "Microfabrication inside capillaries using multiphase laminar flow patterning" Science (Jul. 2, 1999);285(5424):83-85.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kozarewa, et al, "96-plex molecular barcoding for the Illumina Genome Analyzer", Methods Mol Biol., 733:279-98, 2011.
Kozarewa, I. et al. "Amplification-free Illumina sequencing-library preparation facilitates improved mapping and assembly of GC-biased genomes", Nat Methods., 6: 291-5, 2009.
Kwok et al, "Single-molecule analysis for molecular haplotyping", Hum Mutat., 23:442-6, 2004.
Lagally, E.T. et al. "Single-Molecule DNA Amplification and Analysis in an Integrated Microfluidic Device" Anal. Chem. (2001) 73(3):565-570.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. 2017 May 29, 2017. doi: 10.1038/nbt.3880. [Epub ahead of print].
Lennon et al. "A scalable, fully automated process for construction of sequence-ready barcoded libraries for 454." Genome Biology 11:R15 (201 O).
Lienemann, P.S. et al. "Single cell-laden protease-sensitive microfiches for long-term culture in 3D" LabChip (2017) 17(4):727-737.
Linch, et al. Bone marrow processing and cryopreservation. Journal of Clinical Pathology; Feb. 1982, vol. 35, No. 2; pp. 186-190.
Lo, et al. On the design of clone-based haplotyping. Genome Biol. 2013;14(9):R100.
Lundin, et al, "Hierarchical molecular tagging to resolve long continuous sequences by massively parallel sequencing", Sci Rep., 3:1186, 2003.
MacAulay, et al. Single-Cell Multiomics: Multiple Measurements from Single Cells. Trends in Genetics 33.2 (2017): 155-168. PMC. Web. Dec. 18, 2017.
MacAulay; et al., "G&T-seq: parallel sequencing of single-cell genomes and transcriptomes." Nature Methods, 2015, p. 1-7.
Man, P. "Monolithic structures for integrated microfluidic analysis" (2001) Dissertation.
Maricic, T. et al. "Optimization of 454 sequencing library preparation from small amounts of DNA permits sequence letermination of both DNA strands" Biotechniques. Jan. 2009; 46(1 ):51-2, 54-7.
MiRNA (http://www.exiqon.com/what-are-microRNAs) accessed Oct. 19, 2017 (Year: 2017).
Morgan, et al. Chapter 12: Human microbiome analysis. PLoS Comput Biol. 2012;8(12):e1002808. doi: 10.1371/journal.pcbi.1002808. Epub Dec. 27, 2012.
Myllykangas et al., Targeted Sequencing Library Preparation by Genomic DNA Circularization, BMC Biotechnology, 2011, 11(122), 1-12.
Nisisako, T. et al. "Droplet formation in a microchannel network " Lab on a Chip (2002) 2:24-26.
Nisisako, T. et al. "Droplet Formation in a Microchannel on PMMA Plate" Abstract.
Orakdogen, N. "Novel responsive poly(N,N-dimethylaminoethyl methacrylate) gel beads: preparation, mechanical properties and pH-dependent swelling behavior" J Polym Res (2012) 19:9914 (Year: 2012).

(56) References Cited

OTHER PUBLICATIONS

Oyola, et al, "Optimizing Illumina next-generation sequencing library preparation for extremely AT-biased genomes", BMC Genomics. ,13:1, 2012.
PCT/IB2010/002243, International Search Report and Written Opinion, dated Feb. 9, 2011, 13pgs.
Perrott, Jimmy. Optimization and Improvement of Emulsion PCR for the Ion Torrent Next-Generation Sequencing Platform. (2011) Thesis.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Rakszewska, A. et al. "One drop at a time: toward droplet microfluidics as a versatile tool for single-cell analysis" NPG Asia Materials (2014) 6(10):e133 (12 pages).
Ramsey, J.M. "The burgeoning power of the shrinking laboratory" Nature Biotech (1999) 17:1061-1062.
Ramskold et al. "Full-length mRNA-Seq from single-cell levels of RNA and individual circulating tumor cells" Nature Biotech (2012) 30(8):777-782.
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Roche "Using Multiplex Identifier (MID) Adaptors for the GS FLX Titanium Chemistry Basic MID Set" Genome Sequencer FLX System, Technnical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche "Using Multiplex Identifier (MID) Adaptors for the GS FLX Titanium Chemistry Extended MID Set" Genome Sequencer FLX System, Technnical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.
Rodrigue, S. et al. "Whole Genome Amplification and De novo Assembly of Single Bacterial Cells" PLoS ONE, (2009) 4(9):1-10.
Schubert, et al. "Microemulsifying fluorinated oils with mixtures of fluorinated an hydrogenated surfactants" Colloids and Surfaces A: Physicochemical and Engineering Aspects (1994) 84:97-106.
"Portable Water Filters" (http://www.portablewaterfilters.org/water-filter-guide/particle-contaminant-size-chart-microns/) 2015, accessed Oct. 19, 2017. (Year: 2015).
Adey, et al. Rapid, low-input, low-bias construction of shotgun fragment libraries by high-density in vitro transposition. Genome Biology 11 :R119 (2010).
Ahern, "Biochemical, Reagents Kits Offer Scientists Good Return on Investment" The Scientist (1995) 9(15):1-7.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi:10.1038/nbt.3662. Epub Aug. 29, 2016.
Boulanger, et al, "Massively parallel haplotyping on microscopic beads for the high-throughput phase analysis of single molecules", PLoS One, vol. 7:1-10, 2012.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brown, K., Targeted Sequencing Using Droplet-Based Microfluidics, RainDance Technologies, 2009, 1-18.
Buchman, GW et al. "Selective RNA amplification: a novel method using dUMP-containing primers and uracil DNA glycosylase" PCR Methods Appl. Aug. 1993; 3(1):28-31.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatoryvariation. Nature. Jul. 23, 2015;523(7561):486-90. doi: 10.1038/nature14590. Epub Jun. 17, 2015.
Burns, J.R. et al. "The intensification of rapid reactions in multiphase systems using slug flow in capillaries" Lab Chip. (Sep. 2001) 1(1):10-15.
Burns, M.A. et al. "An Integrated Nanoliter DNA Analysis Device" Science (1998) 282:484-487.
Burns, M.A. et al. "Microfabricated structures for integrated DNA analysis" PNAS (1996) 93(11):5556-5561.
Caruccio, N., "Preparation of Next-Generation Sequencing Libraries Using Nextera Technology: Simultaneous DNA Fragmentation and Adaptor Tagging by In Vitro Transposition." Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15)11367-11373.
Clark, et al. Single-cell epigenomics: powerful new methods for understanding gene regulation and cell identity. Genome Biol. Apr. 18, 2016;17:72. doi: 10.1186/s13059-016-0944-x.
Co-pending U.S. Appl. No. 15/588,519, filed May 5, 2017.
Co-pending U.S. Appl. No. 15/596,754, filed May 16, 2017.
Co-pending U.S. Appl. No. 15/598,898, filed May 18, 2017.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/693,374, filed Aug. 31, 2017.
Co-pending U.S. Appl. No. 15/717,840, filed Sep. 27, 2017.
Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/719,459, filed Sep. 28, 2017.
Co-pending U.S. Appl. No. 15/720,085, filed Sep. 29, 2017.
Co-pending U.S. Appl. No. 15/825,740, filed Nov. 29, 2017.
Co-pending U.S. Appl. No. 15/831,726, filed Dec. 5, 2017.
Co-pending U.S. Appl. No. 15/831,847, filed Dec. 5, 2017.
Co-pending U.S. Appl. No. 15/832,183, filed Dec. 5, 2017.
Co-pending U.S. Appl. No. 15/832,547, filed Dec. 5, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Curcio, M. "Improved Techniques for High-Throughput Molecular Diagnostics" Royal Institute of Technology (2002) Ph.D. Thesis.
Cusanovich, et al. Supplementary materials for Multiplex single-cell profiling of chromatin accessibility by combinatorial cellular indexing. Science. May 22, 2015;348(6237):910-4. doi:10.1126/science.aab1601. Epub May 7, 2015.

(56) References Cited

OTHER PUBLICATIONS

Cusanovich; et al., "Multiplex single-cell profiling of chromatin accessibility by combinatorial cellular indexing." Sciencexpress, May 7, 2014, p. 1-9.
Damean, N. et al. "Simultaneous measurement of reactions in microdroplets filled by concentration gradients" Lab Chip (Jun. 21, 2009) 9(12):1707-1713.
Dey, et al. "Integrated Genome and Transcriptome Sequencing from the Same Cell." Nature biotechnology 33.3 (2015): 285-289. PMC. Web. Dec. 18, 2017.
Invitrogen Dynal. Dynabeads M-280 Streptavidin 2006 product sheet.
Joneja, A. et al. "Linear nicking endonuclease-mediated strand-displacement DNA amplification" Anal Biochem (2011) 414:58-69.
JPK "Determining the elastic modulus of biological samples using atomic force microscopy" (https://www.jpk.com/app-technotes-img/AFM/pdf/jpk-app-elastic-modulus. 14-1.pdf) 2009, pp. 1-9 (Year: 2009).
Knapp, M. et al. "Generating barcoded libraries for multiplex high-throughput sequencing" Methods Mol Biol (2012) 840:155-170 Epub Dec. 8, 2011.
Kolodeziejczyk et al., "The technology and biology of single-cell RNA sequencing", Molecular Cell, vol. 58 (May 21, 2015).
Lai, H-H et al. "Characterization and use of laser-based lysis for cell analysis on-chip" J.R. Soc. Interface (2008) 5:S113-S121.
Lander, et al. Initial sequencing and analysis of the human genome. Nature, 409 (Feb. 15, 2001): 860-921.
Lasken et al. "Archaebacterial DNA Polymerases Tightly Bind Uracil-containing DNA" The Journal of Biological Chemistry (1996) 271 (30):17692-17696.
Lebedev, A. et al. "Hot Start PCR with heat-activatable primers: a novel approach for improved PCR performance" NAR (2008) 36(20):E131-1.
Lee, K. Y. et al. "Alginate: properties and biomedical applications" Prog Polym Sci. Jan. 2012; 37(1): 106-126.
Margulies 2005 Supplementary methods (Year: 2005).
Margulies et al. "Genome sequencing in microfabricated high-density picoliter reactors", Nature (2005) 437:376-380.
McGinnis, C.S. et al. "Multi-seq: Scalable sample multiplexing for single-cell RNA sequencing using lipi-tagged indices" bioRxiv (2018) doi: http://dx.doi.org/10.1101/387241.
Meyer, et al., From micrograms to picograms: quantitative PCR reduces the material demands of high-throughput sequencing, Nucleic Acids Research, 2008, vol. 36, No. 1, 6 pages.
Miller-Stephenson Chemicals 157 FS Series catalog, www.miller-stephenon.com.
Morimoto, Y. et al. "Monodisperse semi-permeable microcapsules for continuous observation of cells" LabChip (2009) 9(15):2217-2223.
Morton. Parameters of the human genome. Apr. 23, 1991. Proceedings of the National Academy of Sciences of the United States of America, 88: 7474-7476.
Narayanan, J. et al. "Determination of agarose gel pore size: Absorbance measurements vis a vis other techniques" Journal of Physics: Conference Series 28 (2006) 83-86.
National Human Genome Research Institute (NHGRI). The Human Genome Project Completion: Frequently Asked Questions. Last Updated: Oct. 30, 2010.
Park. ChIP-seq: advantages and challenges of a maturing technology. Nature Reviews Genetics vol. 10, pp. 669-680 (2009).
Qiagen. Omniscript Reverse Transcription Handbook. Oct. 2010.
Sakaguchi et al. "Cautionary Note on the Use of dUMP-Containing PGR Primers with Pfu and VentR". BioTechniques (1996) 21(3):369-370.
Savva et al. "The structural basis of specific base excision repair by uracil-DNA glycosylase" Nature (1995) 373:487-493.
Seiffert, et al. Microfluidic fabrication of smart microgels from macromolecular precursors. 2010. Polymer.
Shaikh, et al. A modular microfluidic architecture for integrated biochemical analysis. Proc Natl Acad Sci U S A. Jul. 12, 2005;102(28):9745-50. Epub Jun. 28, 2005.
Simon, et al., "Using formaldehyde-assisted isolation of regulatory elements (FAIRE) to isolate active regulatory DNA", Nature Protocols, 2012, 7(2): 256-267.
Smith, A.M. et al. "Highly-multiplexed barcode sequencing: an efficient method for parallel analysis of pooled samples" Nucl Acids Res (2010) 38(13):e142 Epub May 11, 2010.
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Spormann Laboratory, Polymerase Chain Reaction (PCR), Alfred Spormann Laboratory, 2009, 1-3.
Thaxton, C.S. et al. "A Bio-Bar-Code Assay Based Upon Dithiothreitol Oligonucleotide Release" Anal Chem (2005) 77:8174-8178.
ThermoFisher, Protocols, M-270 Streptavidin, ThermoFisherScientific, 2007, 1-5. (Year: 2007).
Ullal, A.V. et al. "Cancer cell profiling by barcoding allows multiplexed protein analysis in fine needle aspirates" Sci Transl Med (2014) 6(219):219ra9.
Wong, et al. "Multiplexed Barcoded CRISPR-Cas9 Screening Enabled by CombiGEM" PNAS (2016) 113:2544-2549.
Xia and Whitesides, Soft Lithography, Angew. Chem. Int. Ed. 37:550-575 (1998).
Zentner, et al. Surveying the epigenomic landscape, one base at a time. Genome Biol. Oct. 22, 2012;13(10):250. doi: 10.1186/gb4051.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zhou, Y. et al. "Development of an enzyme activity screening system for (3-glucosidase-displaying yeasts using calcium alginatemicrobeads and flow sorting" Appl Microbiol Biotechnol (2009) 84:375-382.
Zhu, YY et al. "Reverse transcriptase template switching: a SMART approach for full-length cDNA library construction" Biotechniques (2001) 30(4):892-897.
"How many species of bacteria are there" (wisegeek.com; accessed Jan. 21, 2014).
"List of sequenced bacterial genomes" (Wikipedia.com; accessed Jan. 24, 2014).
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilizedperturb-seq-approach/.
Adamson et al., "Production of arrays of chemically distinct nanolitre plugs via repeated splitting in microfluidic devices", Lab Chip 6(9): 1178-1186 (Sep. 2006).
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adey, et al., "Ultra-low-input, tagmentation-based whole-genome bisulfite sequencing", Genome Research, 2012, 22 ;6): 1139-1143.
Agasti, S.S. et al. "Photocleavable DNA barcode-antibody conjugates allow sensitive and multiplexed protein analysis in single cell" J Am Chem Soc (2012) 134(45):18499-18502.
Anonymous: "TCEP=HCl" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Ason et al. DNA sequence bias during Tn5 transposition. Journal of molecular biology 335.5 (2004): 1213-1225.
Bjornsson et al., Intra-individual change over time in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.

(56) References Cited

OTHER PUBLICATIONS

Brenner, et al. "In vitro cloning of complex mixtures of DNA on microbeads: physical separation of differentially expressed cDNAs." Proc Natl Acad Sci U S A. Feb. 15, 2000;97(4):1665-70.
Caruccio et al. "Nextera Technolgoy for NGS DNA Library Preparation: Simultaneous Fragmentation and Tagging by In Vitro Transposition" Nextera Technology, 2009 16-3, 1-3 (Year: 2009).
Chang et al. "Droplet-based microfluidic platform for heterogeneous enzymatic assays" LabChip (2013) 13:1817-1822.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Co-pending U.S. Appl. No. 16/033,065, filed Jul. 11, 2018.
Co-pending U.S. Appl. No. 16/043,874, filed Jul. 24, 2018.
Co-pending U.S. Appl. No. 16/044,374, filed Jul. 24, 2018.
Co-pending U.S. Appl. No. 16/045,474, filed Jul. 25, 2018.
Co-pending U.S. Appl. No. 16/052,431, filed Aug. 1, 2018.
Co-pending U.S. Appl. No. 16/052,486, filed Aug. 1, 2018.
Co-pending U.S. Appl. No. 16/056,231, filed Aug. 6, 2018.
Co-pending U.S. Appl. No. 16/107,685, filed Aug. 21, 2018.
Co-pending U.S. Appl. No. 16/138,448, filed Sep. 21, 2018.
Co-pending U.S. Appl. No. 16/144,832, filed Sep. 27, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/206,168, filed Nov. 30, 2018.
Delehanty, et al. Peptides for specific intracellular delivery and targeting of nanoparticles: implications for developing nanoparticle-mediated drug delivery. Ther Deilv. Sep. 2010;1(3):411-33.
Depristo, M.A. et al. "A framework for variation discovery and genotyping using next-generation DNA sequencing data" Nature Genetics (2011) 43(5):491-498.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
EP14800805.5 Extended Search Report dated Jan. 23, 2017.
Epicentre., "EZ-Tn5TM Custom Transposome Construction Kits", http://www.epicentre.com, pp. 1-17, 2012.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymerd-DNA Hybrid Hydrogel, Royal Soc. Chem. 7:1741-1746 (Dec. 20, 2010).
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Han, S-E et al. "Targeted Sequencing of Cancer-Related Genes in Colorectal Cancer Using Next-Generation Sequencing" PLOS One (2013) 8(5):e64271.
Haring, et al. Chromatin immunoprecipitation: optimization, quantitative analysis and data normalization. Plant Methods. 2007; 3: 11.
Holmberg, et al. The biotin-streptavidin interaction can be reversibly broken using water at elevated temperatures. Feb. 2, 2005. Electrophoresis, 26:501-510.
Hu et al., Shape Controllable Microgel Particles Prepared by Microfluidic Combining External Crosslinking, Biomicrofluidics 6:26502 (May 18, 2012).
International Search Report for International Patent Application No. PCT/US2016/064611 dated Apr. 4, 2017, 21 pages.
Biles et al., Nucl. Acids Res. 32(22):e176 2004.
Christian M, et al. Targeting DNA double-strand breaks with TAL effector nucleases Genetics. (2010) 186:757-761.
Cong et al., "Multiplex Genome Engineering Using CRISPR/Cas Systems," Science, Feb. 15, 2013, vol. 339, No. 6121, pp. 819-823.
Co-pending U.S. Appl. No. 15/392,557, filed Dec. 28, 2016.
Co-pending U.S. Appl. No. 15/430,298, filed Feb. 10, 2017.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Fan, et al. "Whole-genome molecular haplotyping of single cells," Nature Biotechnology, vol. 29 No. 1, Jan. 2011.
Kivioj, A. et al., "Counting Absolute Numbers of Molecules Using Unique Molecular Identifiers", Nature Methods 9, 72-74 (2012).
Korlach, et al., Methods in Enzymology, Real-Time DNA Sequencing from Single Polymerase Molecules, (2010) 472:431-455.
Lee et al., "Highly Multiplexed Subcellular RNA Sequencing in Situ," Science, Author Manuscript, Sep. 21, 2014, col. 343, pp. 1-12.
Li, et al. A single-cell-based platform for copy number variation profiling through digital counting of amplified genomic DNA fragments. ACS Appl Mater Interfaces. Mar. 24, 2017. doi:10.1021/acsami.7b03146. [Epub ahead of print].
Miller, J.C. et al. An improved zinc-finger nuclease architecture for highly specific genome editing. Nat. Biotechnol. 2007;25:778-785.
Nagano et al. "Single cell Hi-C reveals cell-to-cell variability in chromosome structure," Nature, vol. 502, No. 7469, Sep. 25, 2013.
Picot, J. et al. "A biomimetic microfluidic chip to study the circulation and mechanical retention of red blood cells in the spleen" Am J Hematology (Jan. 12, 2015) 90(4):339-345.
Porteus, M.H., Baltimore D. Chimeric nucleases stimulate gene targeting in human cells. Science. 2003;300:763.
Ran, et al., Genome Engineering Using the CRISPR-Cas9 System, Nature Protocol, (2013), 8(11):2281-2308.
Rotem, A. et al. "Single-cell ChIP-seq reveals cell subpopulations defined by chromatin state" Nature Biotech (Oct. 12, 2015) 33(11):1165-1172.
Sander JD, et al. Selection-free zinc-finger-nuclease engineering by context-dependent assembly (CoDA). Nat. Methods. 2011;8:67-69.
Wood AJ, et al. Targeted genome editing across species using ZFNs and TALENs. Science. 2011;333:307.
Zhang F, et al. Efficient construction of sequence-specific TAL effectors for modulating mammalian transcription. Nat. Biotechnol. 2011;29:149-153.
Zhu et al. Hydrogel Droplet Microfluidics for High-Throughput Single Molecule/Cell Analysis. Accounts of Chemical Research Article ASAP. DOI: 10.1021 /acs.accounts.6b00370.
Schwartz; et al., "Capturing native long-range contiguity by in situ library construction and optical sequencing", PNAS (Nov. 2012), 109(46)18749-18754.
Shahi, et al. Abseq: Ultrahigh-throughput single cell protein profiling with droplet microfluidic barcoding. Sci Rep. 2017; 7: 44447 Published online Mar. 14, 2017. doi: 10.1038/srep44447.
Skerra, A. "Phosphorothioate primers improve the amplification of DNA sequences by DNA polymerases with proofreading activity" Nucleic Acids Res. Jul. 25, 1992; 20(14):3551-4.
Song, H. et al. "Reactions in Droplets in Microfluidic Channels" Angew. Chem. Int. Ed. (2006) 45:7336-7356.
Stoeckius et al. "Simultaneous epitope and transcriptome measurement in single cells" Nature Methods (Jul. 31, 2017) Supplemental Materials.
Stoeckius, et al. "Large-scale simultaneous measurement of epitopes and transcriptomes in single cells." bioRxiv 113068; doi: https://doi.org/10.1101/113068.
Syed, F. et al. Nature Methods (Nov. 2009) 2 pages.
Tewhey et al., Supplementary Materials, Nature Biotechnology, 2009, 27(11), 1-22.
Thorsen, T. et al. "Dynamic Pattern Formation in a Vesicle-Generating Microfluidic Device" Phys Rev Letts (Apr. 30, 2001) 86(18):4163-4166.
Turner, et al, "Assaying chromosomal inversions by single molecule haplotyping", Nat Methods., 3:439-445, 2006.

(56) References Cited

OTHER PUBLICATIONS

Turner, et al, "High-throughput haplotype determination over long distances by haplotype fusion PCR and ligation haplotyping", Nat Protoc., 4:1771-83, 2009.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wang; et al., "Self-Formed Adaptor PCR: a Simple and Efficient Method for Chromosome Walking", Applied and Environmental Microbiology (Aug. 2007), 73(15):5048-5051.
Ward, T. et al. "Microfluidic flow focusing: drop size and scaling in pressure versus flow-rate-driven pumping" Electrophoresis (2005) 26(19):3716-3724.
Weigl, B.H. et al. "Microfluidic Diffusion-Based Separation and Detection" Science (Jan. 15, 1999) 283(5400):346-347.
Wiseman, R.W. et al. "Major histocompatibility complex genotyping with massively parallel pyrosequencing" Nature Medicine (Oct. 11, 2009) 15(11):1322-1326.
Xi, L. et al. "New library construction methods for single-cell genomes" PLOS (2017) 12(7):e0181163.
Xiao, et al, "Determination of haplotypes from single DNA molecules: a method for single-molecule barcoding", Hum Mutat., 28:913-21, 2007.
Yan, Pu et al. "Rapid on-step construction of hairpin RNA" Biochem and Biophys Res Comm (Jun. 12, 2009) 383(4):464-468.
Zeng, Y. et al. "High-Performance Single Cell Genetic Analysis Using Microfluidic Emulsion Generator Arrays" Analytical Chemistry (Apr. 15, 2010) 82(8):3183-3190.
Zerbino, Daniel, "Velvet Manual—version 1.1," Aug. 15, 2008, pp. 1-22.
Zhang. Genomics of inherited bone marrow failure and myelodysplasia. Dissertation [online]. University of Washington. 2015 [Retrieved on May 3, 2017].
Zheng, et al. Massively parallel digital transcriptional profiling of single cells. Nat Commun. Jan. 16, 2017;8:14049. doi: 10.1038/ncomms14049.
Stahl et al., "Visualization and analysis of gene expression in tissue sections by spatial transcriptions", Science, Jul. 1, 2016, vol. 353, No. 6294, pp. 78-82.

* cited by examiner

METHODS AND COMPOSITIONS FOR NUCLEIC ACID ANALYSIS

CROSS REFERENCE TO RELATED APPLICATIONS

This application claims the benefit of U.S. Provisional Application No. 62/263,532, filed Dec. 4, 2015, which is hereby incorporated by reference in its entirety for all purposes.

BACKGROUND OF THE INVENTION

Polynucleotide sequencing continues to find increasing use in medical applications such as genetic screening and genotyping of tumors. Many polynucleotide sequencing methods rely on sample processing techniques of the original sample, including random fragmentation of polynucleotides. These processing techniques can provide advantages in terms of throughput and efficiency, but the resultant sequence information obtained from these processed samples can lack important contextual information in terms of the location of particular sequences within the broader linear (two-dimensional) sequence of the original nucleic acid molecule that contained those sequences. Structural context within the three dimensional space of the original sample is also lost with many sample processing and sequencing techniques. There is thus a need for sequencing technologies that retain structural and molecular context of the identified nucleic acid sequences.

SUMMARY OF THE INVENTION

Accordingly, the present invention provides methods, systems and compositions for providing sequence information that retains both molecular and structural context of the originating nucleic acid molecule.

In some aspects, the present disclosure provides methods of analyzing nucleic acids while maintaining structural context. Such methods include the steps of: (a) providing a sample containing nucleic acids, where the nucleic acids comprise three dimensional structures; (b) separating portions of the sample into discrete partitions such that portions of the nucleic acid three dimensional structures are also separated into the discrete partitions; (c) obtaining sequence information from the nucleic acids, thereby analyzing nucleic acids while maintaining structural context.

In some embodiments, the sequence information from obtaining step (c) includes identification of nucleic acids that are in spatial proximity to each other.

In further embodiments, the sequence information from obtaining step (c) includes identification of nucleic acids that are in spatial proximity to each other.

In still further embodiments, the obtaining step (c) provides information on intrachromosomal and/or interchromosomal interactions between genomic loci.

In yet further embodiments, the obtaining step (c) provides information on chromosome conformations.

In further embodiments, prior to separating step (b), at least some of the three dimensional structures are processed to link different portions of the nucleic acids that are in proximity to each other within the three dimensional structures.

In any embodiments, the nucleic acids are not isolated from the sample prior to the separating step (b).

In any embodiments, prior to the obtaining step (c), the nucleic acids within the discrete partitions are barcoded to form a plurality of barcoded fragments, where fragments within a given discrete partition each comprise a common barcode, such that the barcodes identify nucleic acids from a given partition.

In further embodiments, the obtaining step (c) comprises a sequencing reaction selected from the group consisting of: short read-length sequencing reactions and long read-length sequencing reactions.

In some aspects, the present disclosure provides methods of analyzing nucleic acids while maintaining structural context that include the steps of: (a) forming linked nucleic acids within the sample such that spatially adjacent nucleic acid segments are linked; (b) processing the linked nucleic acids to produce a plurality of ligation products, wherein the ligation products contain portions of the spatially adjacent nucleic acid segments; (c) depositing the plurality of ligation products into discrete partitions; (d) barcoding the ligation products within the discrete partitions to form a plurality of barcoded fragments, wherein fragments within a given discrete partition each comprise a common barcode, thereby associating each fragment with the linked nucleic acid from which it is derived; (e) obtaining sequence information from the plurality of barcoded fragments, thereby analyzing nucleic acids from the sample while maintaining structural context.

In some aspects, the present disclosure provides methods of analyzing nucleic acids while maintaining structural context that include the steps of: (a) forming linked nucleic acids within the sample such that spatially adjacent nucleic acid segments are linked; (b) depositing the linked nucleic acids into discrete partitions; (c) processing the linked nucleic acids to produce a plurality of ligation products, wherein the ligation products contain portions of the spatially adjacent nucleic acid segments; (d) barcoding the ligation products within the discrete partitions to form a plurality of barcoded fragments, wherein fragments within a given discrete partition each comprise a common barcode, thereby associating each fragment with the linked nucleic acid from which it is derived; (e) obtaining sequence information from the plurality of barcoded fragments, thereby analyzing nucleic acids from the sample while maintaining structural context.

In some aspects, the present disclosure provides methods of analyzing nucleic acids while maintaining structural context that include the steps of (a) cross-linking nucleic acids within the sample to form cross-linked nucleic acids, wherein the cross-linking forms covalent links between spatially adjacent nucleic acid segments; (b) depositing the cross-linked nucleic acids into discrete partitions; (c) processing the cross-linked nucleic acids to produce a plurality of ligation products, wherein the ligation products contain portions of the spatially adjacent nucleic acid segments; (d) obtaining sequence information from the plurality of ligation products, thereby analyzing nucleic acids from the sample while maintaining structural context.

In any embodiments, the sample is a formalin-fixed paraffin sample.

In any embodiments, the discrete partitions comprise beads. In further embodiments, the beads are gel beads.

In any embodiments, the sample comprises a tumor sample.

In any embodiments, the sample comprises a mixture of tumor and normal cells.

In any embodiments, the sample comprises a nuclear matrix.

In any embodiments, the nucleic acids comprise RNA.

In any embodiments, the amount of nucleic acids in the sample is less than 5, 10, 15, 20, 25, 30, 35, 40, 45, or 50 ng/ml.

In some aspects, the present invention provides a method of analyzing nucleic acids while maintaining structural context, in which the method includes the steps of: (a) providing a sample that contains nucleic acids; (b) applying a library of tags to the sample such that different geographical regions of the sample receive different tags or different concentrations of tags; (c) separating portions of the sample into discrete partitions such that portions of the library of tags and portions of the nucleic acids are also separated into the discrete partitions; (d) obtaining sequence information from the nucleic acids, and (e) identifying tags or concentrations of tags in the discrete partitions, thereby analyzing nucleic acids while maintaining structural context.

DETAILED DESCRIPTION OF THE INVENTION

Figure 1:
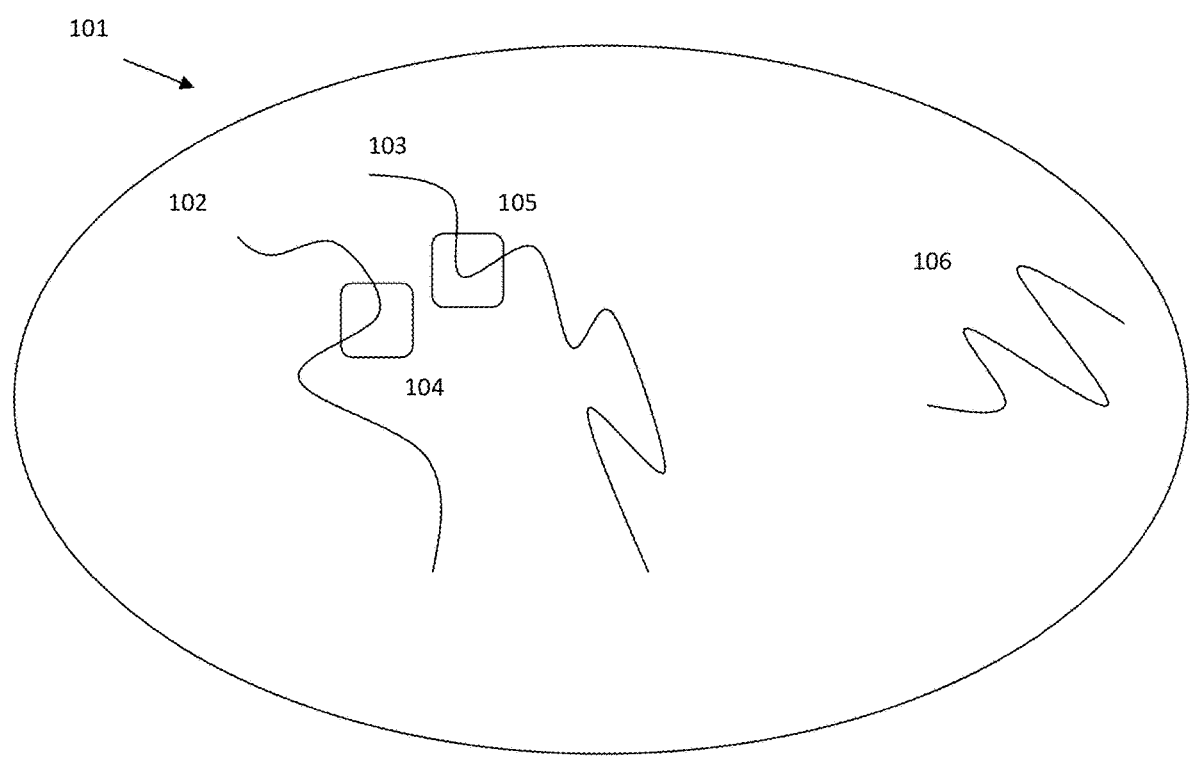
FIG. 1 provides a schematic illustration of molecular context and structural context in accordance with the methods described herein.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but do not exclude others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

I. OVERVIEW

This disclosure provides methods, compositions and systems for characterization of genetic material. In general, the methods, compositions and systems described herein provide methods of analyzing components of a sample while retaining information on the structural as well as molecular context of those components as they were originally in the sample. Although much of the discussion herein is in terms of the analysis of nucleic acids, it will be appreciated that the methods and systems discussed herein can be adapted to apply to other components of a sample, including proteins and other molecules.

Deoxyribonucleic acid (DNA) is a linear molecule, and as such the genome is often described and assessed in terms of linear dimensions. However, chromosomes are not rigid, and the spatial distance between two genomic loci need not always correspond to their distance along the linear sequence of the genome. Regions separated by many megabases can be immediately adjacent in 3-dimensional space. From the standpoint of regulation, understanding long-range interactions between genomic loci may be useful. For example, gene enhancers, silencers, and insulator elements may possibly function across vast genomic distances. The ability to retain both structural and molecular context of sequence reads provides the ability to understand such long-range interactions.

By "retaining structural context" as used herein means that multiple sequence reads or multiple portions of sequence reads are attributable to the original three-dimensional relative location of those sequence reads within the sample. In other words, the sequence reads can be associated with a relative location within the sample with respect to neighboring nucleic acids (and in some situations associated proteins) in that sample. This spatial information is available through the methods discussed herein even if those neighboring nucleic acids are not physically located within the linear sequence of a single originating nucleic acid molecule. Referring to the schematic illustration in FIG. 1: in a sample (101), sequences (104) and (105) are located within the linear sequence of two different originating nucleic acid molecules ((102) and (103) respectively), but are located in spatial proximity to each other within the sample. The methods and compositions described herein provide the ability to retain that information on the structural context of sequence reads and thus allow reads from sequences (104) and (105) to be attributed to their relative spatial proximity within the original sample on the original nucleic acid molecules (102) and (103) from which those sequence reads are derived.

The methods and compositions discussed herein also provide sequence information that retains molecular context. "Retaining molecular context" as used herein means that multiple sequence reads or multiple portions of sequence reads may be attributable to a single originating molecule of a nucleic acid. While this single molecule of a nucleic acid may be of any of a variety of lengths, in preferred aspects, it will be a relatively long molecule, allowing for preservation of long range molecular context. In particular, the single originating molecule is preferably substantially longer than the typical short read sequence length, e.g., longer than 200 bases, and is often at least 1000 bases or longer, 5000 bases or longer, 10,000 bases or longer, 20,000 bases or longer, 30,000 bases or longer, 40,000 bases or longer, 50,000 bases or longer, 60,000 bases or longer, 70,000 bases or longer, 80,000 bases or longer, 90,000 bases or longer, or 100,000 bases or longer, and in some cases up to 1 megabase or longer.

In general, the methods described herein include analyzing nucleic acids while maintaining structural and molecular context. Such analyses include methods in which a sample containing nucleic acids is provided, where the nucleic acids contain three dimensional structures. Portions of the sample are separated into discrete partitions such that portions of the nucleic acid three dimensional structures are also separated into the discrete partitions—nucleic acid sequences that are in spatial proximity to each other will tend to be separated into the same partition, thus retaining the three-dimensional information of that spatial proximity even when later-obtained sequence reads are from sequences that were not originally on the same individual originating nucleic acid molecule. Referring again to FIG. 1: if sample 101, containing nucleic acid molecules 102 and 103 and 106, is separated into discrete partitions such that subsets of the sample are allocated into different discrete partitions, it is more likely that nucleic acid molecules 102 and 103 will be placed in the same partition with each other than with nucleic acid molecule 106, because of the physical distance between nucleic acid molecule 106 and 102 and 103. As such, nucleic acid molecules within the same discrete partitions are those that were in spatial proximity to each other in the original sample. Sequence information obtained from nucleic acids within the discrete partitions thus provides a way to analyze the nucleic acids, for example through nucleic acid sequencing, and attribute those sequence reads back to the structural context of the originating nucleic acid molecules.

In further examples, the structural context (also referred to herein as "geographical context") may be maintained by using tags (such as barcode oligonucleotides) to encode the geography of the sample. In some situations, this can include injecting a viral library encoding a collection of barcoded sequences (such as mRNA sequences) to a sample. The barcodes travel through the sample by active processes or by diffusion. When the sample is then further processed in accordance with methods described herein and known in the art, barcodes can be correlated with structural positions to identify nucleic acid sequences from the same geographic location within the sample. In examples in which the barcodes are distributed through the sample through active processes, sequences with the same barcode may be geographically connected and/or connected through the same process. As will be appreciated, this system of using tags to encode structural context can be used alone or in combination with methods described herein utilizing discrete partitions to further retain structural and molecular context. In examples in which tags for encoding spatial locations and barcodes for identifying molecules separated into the same discrete partitions are used, the samples are in essence tagged or "double barcoded" where one set of barcodes is used for identifying spatial locations and one set of barcodes is partition-specific. In such examples, both sets of barcodes can be used to provide information to retain structural and molecular context of sequence reads generated from the sample.

In some examples, the sequence information obtained from the nucleic acids provides information on intrachromosomal and/or interchromosomal interactions between genomic loci. In further examples, the sequence information includes information on chromosome conformations.

In further examples, prior to separation into the discrete partitions, the nucleic acids in the sample may be processed to link different regions of their three dimensional structures such that regions of the sequence that are in proximity to each other within those three dimensional structures are attached to each other. As such, the separation of the sample into discrete partitions will separate those linked regions into the same partition, thereby further ensuring that the structural context of any sequence reads from those nucleic acids is retained.

In some situations, the linking of nucleic acids may be accomplished using any methods known in the art used to cross-link molecules in spatial proximity. Such cross-linking agents may include without limitation alkylating agents, cisplatin, nitrous oxide, psoralens, aldehydes, acrolein, glyoxal, osmium tetroxide, carbodiimide, mercuric chloride, zinc salts, picric acid, potassium dichromate, ethanol, methanol, acetone, acetic acid, and the like. In specific examples, the nucleic acids are linked using protocols designed for analysis of the three dimensional architecture of genomes, such as the "Hi-C" protocol described for example in Dekker et al., "Capturing chromosome conformation" Science 295:1306-1311 (2002) and Berkum et al., J. Vis. Exp. (39), e1869, doi:10.3791/1869 (2010), which are each hereby incorporated by reference in its entirety for all purposes and in particular for all teachings related to linking nucleic acid molecules. Such protocols generally involve producing a library of molecules by crosslinking the sample so that genomic loci that are in close spatial proximity become linked. In further embodiments, the intervening DNA loop between the crosslink is digested away and then the intrasequence regions are reverse crosslinked for addition to the library. The digesting and reverse crosslinking steps may occur prior to a step of partitioning the sample into discrete partitions, or it may occur within the partitions after the separating step.

In still further examples, the nucleic acids may undergo a tagging or barcoding step that provides a common barcode for all nucleic acids within a partition. As will be appreciated, this barcoding may occur with or without the nucleic acid linking/cross-linking steps discussed above. The use of the barcoding technique disclosed herein confers the unique capability of providing individual structural and molecular context for genomic regions—i.e., by attributing certain sequence reads to individual sample nucleic acid molecules, and through variant coordinated assembly, to provide a broader or even longer range inferred context, among multiple sample nucleic acid molecules, and/or to a specific chromosome. The term "genomic region" or "region" as used herein, refers to any defined length of a genome and/or chromosome. For example, a genomic region may refer to the association (i.e., for example, an interaction) between more than one chromosomes. A genomic region can also encompass a complete chromosome or a partial chromosome. In addition, a genomic region can include a specific nucleic acid sequence on a chromosome (i.e., for example, an open reading frame and/or a regulatory gene) or an intergenic noncoding region.

The use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

In addition to providing the ability to obtain sequence information from entire or select regions of the genome, the methods and systems described herein can also provide other characterizations of genomic material, including without limitation haplotype phasing, identification of structural variations and copy number variations, as described in U.S. Ser. Nos. 14/316,383; 14/316,398; 14/316,416; 14/316,431; 14/316,447; and 14/316,463, which are herein incorporated by reference in their entirety for all purposes and in particular for all written description, figures and working examples directed to characterization of genomic material.

Figure 2:
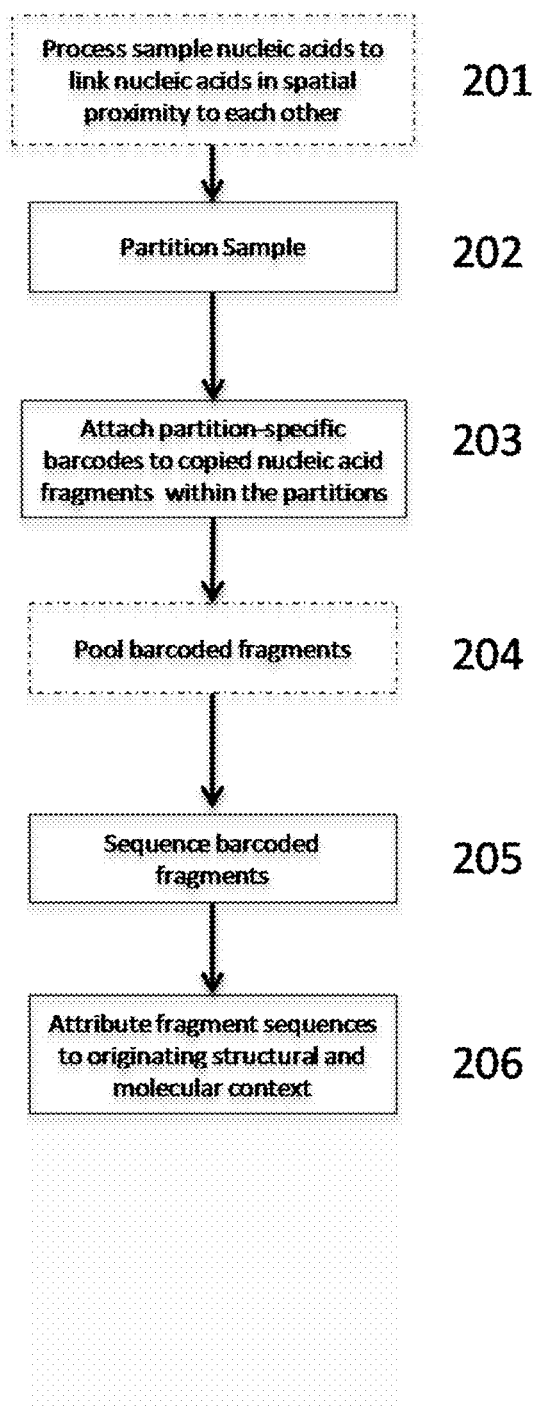
FIG. 2 provides a schematic illustration of a process described herein.

Generally, methods of the invention include steps as illustrated in FIG. 2, which provides a schematic overview of methods of the invention discussed in further detail herein. As will be appreciated, the method outlined in FIG. 2 is an exemplary embodiment that may be altered or modified as needed and as described herein. As shown in FIG. 2, the methods described herein may include an optional step 201 in which sample nucleic acids are processed to link nucleic acids in spatial proximity to each other. With or without that preliminary processing step (201), the methods described herein will in most examples include a step in which sample nucleic acids containing are partitioned (202). Generally, each partition containing nucleic acids from genomic regions of interest will undergo a process that results in fragments containing barcodes (203). Those fragments may then be pooled (204) prior to sequencing (205). The sequence reads from (205) can be attributed to the originating structural and molecular context (206) generally due to the partition-specific barcodes (203). Each partition may in some examples include more than one nucleic acid, and will in some instances contain several hundred nucleic acid molecules. The barcoded fragments of step 203 can be generated using any methods known in the art—in some examples, oligonucleotides are included with the samples within the distinct partitions. Such oligonucleotides may comprise random sequences intended to randomly prime numerous different regions of the samples, or they may comprise a specific primer sequence targeted to prime upstream of a targeted region of the sample. In further examples, these oligonucleotides also contain a barcode sequence, such that the replication process also barcodes the resultant replicated fragment of the original sample nucleic acid. A particularly elegant process for use of these barcode oligonucleotides in amplifying and barcoding samples is described in detail in U.S. Ser. Nos. 14/316,383; 14/316,398; 14/316,416; 14/316,431; 14/316,447; and 14/316,463, each of which is herein incorporated by reference in its entirety for all purposes and in particular for all teachings related to barcoding and amplifying oligonucleotides. Extension reaction reagents, e.g., DNA polymerase, nucleoside triphosphates, co-factors (e.g., $Mg^{2+}$ or $Mn^{2+}$ etc.), that are also contained in the partitions, then extend the primer sequence using the sample as a template, to produce a complementary fragment to the strand of the template to which the primer annealed, and the complementary fragment includes the oligonucleotide and its associated barcode sequence. Annealing and extension of multiple primers to different portions of the sample can result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In further examples, this replication process is configured such that when the first complement is duplicated, it produces two complementary sequences at or near its termini to allow the formation of a hairpin structure or partial hairpin structure, which reduces the ability of the molecule to be the basis for producing further iterative copies. An advantage of the methods and systems described herein is that attaching a partition- or sample-specific barcode to the copied fragments preserves the original molecular context of the sequenced fragments, allowing them to be attributed to their original partition and thus their originating sample nucleic acid molecule.

Often, the sample is combined with a set of oligonucleotide tags that are releasably-attached to beads prior to the partitioning step. Methods for barcoding nucleic acids are known in the art and described herein. In some examples, methods are utilized as described in Amini et al, 2014, *Nature* Genetics, Advance Online Publication), which is herein incorporated by reference in its entirety for all purposes and in particular for all teachings related to attaching barcodes or other oligonucleotide tags to nucleic acids. Methods of processing and sequencing nucleic acids in accordance with the methods and systems described in the present application are also described in further detail in U.S. Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material.

In addition to the above workflow, targeted genomic regions may be enriched, isolated or separated, i.e., "pulled down," for further analysis, particularly sequencing, using methods that include both chip-based and solution-based capture methods. Such methods utilize probes that are complementary to the genomic regions of interest or to regions near or adjacent to the genomic regions of interest. For example, in hybrid (or chip-based) capture, microarrays containing capture probes (usually single-stranded oligonucleotides) with sequences that taken together cover the region of interest are fixed to a surface. Genomic DNA is fragmented and may further undergo processing such as end-repair to produce blunt ends and/or addition of additional features such as universal priming sequences. These fragments are hybridized to the probes on the microarray. Unhybridized fragments are washed away and the desired fragments are eluted or otherwise processed on the surface for sequencing or other analysis, and thus the population of fragments remaining on the surface is enriched for fragments containing the targeted regions of interest (e.g., the regions comprising the sequences complementary to those contained in the capture probes). The enriched population of fragments may further be amplified using any amplification technologies known in the art. Exemplary methods for such targeted pull down enrichment methods are described in U.S. Ser. No. 14/927,297, filed on Oct. 29, 2015, which is hereby incorporated by reference in its entirety for all purposes and in particular for all teachings related to targeted pull down enrichment methods and sequencing methods, including all written description, figures and examples. The population of targeted genomic regions may further be enriched prior to the above-described pull-down methods by using methods to increase coverage of those targeted regions. Such increased coverage may for example be accomplished using targeted amplification methods, including those described for example in U.S. Ser. No. 62/119,996, filed on Feb. 24, 2015, which is hereby incorporated by reference for all purposes and in particular for all teachings related to targeted coverage of nucleic acid molecules.

In specific instances, methods described herein include a step in which selected regions of the genome are selectively amplified prior to sequencing. This amplification, which is generally conducted using methods known in the art (including without limitation PCR amplification) provides at least 1×, 10×, 20×, 50×, 100×, 200×, 500×, 1000×, 1500×, 2000×, 5000×, or 10000× coverage of the selected regions of the genome, thereby providing a quantity of nucleic acids to allow de novo sequencing of those selected regions. In further embodiments, the amplification provides at least 1×-20×, 50×-100×, 200×-1000×, 1500×-5000×, 5000×-10,000×, 1000×-10000×, 1500×-9000×, 2000×-8000×, 2500×-7000×, 3000×-6500×, 3500×-6000×, 4000×-5500× coverage of the selected regions of the genome.

The amplification is generally conducted through extension of primers complementary to sequences within or near the selected regions of the genome. In some cases, a library of primers is used that is designed to tile across the regions of interest—in other words, the library of primers is designed to amplify regions at specific distances along the selected regions of the genome. In some instances, the selective amplification utilizes primers that are complementary to every 10, 15, 20, 25, 50, 100, 200, 250, 500, 750, 1000, or 10000 bases along the selected regions of the genome. In still further examples, the tiled library of primers is designed to capture a mixture of distances—that mixture can be a random mixture of distances or intelligently designed such that specific portions or percentages of the selected regions are amplified by different primer pairs. Further information of targeted coverage of the genome for use in accordance with methods described herein is provided for example in U.S. Ser. No. 62/146,834, filed on Apr. 13, 2015, which is hereby incorporated by reference in its entirety for all purposes, and in particular for all teachings related to targeted coverage of a genome.

In general, the methods and systems described herein provide nucleic acids for analyses such as sequencing. Sequencing information is obtained using methods that have the advantages of the extremely low sequencing error rates and high throughput of short read sequencing technologies. As described above, the sequencing of nucleic acids is typically carried out in a manner that preserves the structural and molecular context of sequence reads or portions of sequence reads. By that is meant that multiple sequence reads or multiple portions of sequence reads may be attributable to the spatial location relative to other nucleic acids in the original sample (structural context) and to the location of that sequence read along the linear sequence of a single originating molecule of a nucleic acid (molecular context). While this single molecule of a nucleic acid may be of any of a variety of lengths, in preferred aspects, it will be a relatively long molecule, allowing for preservation of long range molecular context. In particular, the single originating molecule is preferably substantially longer than the typical short read sequence length, e.g., longer than 200 bases, and is often at least 1000 bases or longer, 5000 bases or longer, 10,000 bases or longer, 20,000 bases or longer, 30,000 bases or longer, 40,000 bases or longer, 50,000 bases or longer, 60,000 bases or longer, 70,000 bases or longer, 80,000 bases or longer, 90,000 bases or longer, or 100,000 bases or longer, and in some cases up to 1 megabase or longer.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. As will be appreciated, by providing long range individual molecular context, one can also derive the phasing information of variants within that individual molecular context, e.g., variants on a particular long molecule will be, by definition commonly phased.

By providing longer range individual molecular context, the methods and systems of the invention also provide much longer inferred molecular context (also referred to herein as a "long virtual single molecule read"). Sequence context, as described herein can include mapping or providing linkage of fragments across different (generally on the kilobase scale) ranges of full genomic sequence. These methods include mapping the short sequence reads to the individual longer molecules or contigs of linked molecules, as well as long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

Furthermore, while one may utilize the long range sequence context associated with long individual molecules, having such long range sequence context also allows one to infer even longer range sequence context. By way of one example, by providing the long range molecular context described above, one can identify overlapping variant portions, e.g., phased variants, translocated sequences, etc., among long sequences from different originating molecules, allowing the inferred linkage between those molecules. Such inferred linkages or molecular contexts are referred to herein as "inferred contigs". In some cases when discussed in the context of phased sequences, the inferred contigs may represent commonly phased sequences, e.g., where by virtue of overlapping phased variants, one can infer a phased contig of substantially greater length than the individual originating molecules. These phased contigs are referred to herein as "phase blocks".

By starting with longer single molecule reads (e.g., the "long virtual single molecule reads" discussed above), one can derive longer inferred contigs or phase blocks than would otherwise be attainable using short read sequencing technologies or other approaches to phased sequencing. See, e.g., published U.S. Patent Application No. 2013-0157870. In particular, using the methods and systems described herein, one can obtain inferred contig or phase block lengths having an N50 (where the sum of the block lengths that are greater than the stated N50 number is 50% of the sum of all block lengths) of at least about 10 kb, at least about 20 kb, at least about 50 kb. In more preferred aspects, inferred contig or phase block lengths having an N50 of at least about 100 kb, at least about 150 kb, at least about 200 kb, and in many cases, at least about 250 kb, at least about 300 kb, at least about 350 kb, at least about 400 kb, and in some cases, at least about 500 kb or more, are attained. In still other cases, maximum phase block lengths in excess of 200 kb, in excess of 300 kb, in excess of 400 kb, in excess of 500 kb, in excess of 1 Mb, or even in excess of 2 Mb may be obtained.

In one aspect, and in conjunction with any of the methods described above and later herein, the methods and systems described herein provide for the compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned sample nucleic acids, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions. This later attribution further allows attribution to the original structural context of those sample nucleic acids in the original sample, because nucleic acids that were close to each other within the three dimensions of the original sample will be more likely to be deposited into the same partition. Thus, attribution of sequence reads to the partitions (and the nucleic acids contained within those partitions) not only provides a molecular context as to the linear location along the original nucleic acid molecule from which that sequence read was derived, but also provides a structural context of identifying sequence reads from nucleic acids that were in close spatial proximity to each other in the three dimensional context of the original sample.

The sample nucleic acids utilized in the methods described herein typically represent a number of overlapping portions of the overall sample to be analyzed, e.g., an entire chromosome, exome, or other large genomic portion. These sample nucleic acids may include whole genomes, individual chromosomes, exomes, amplicons, or any of a variety of different nucleic acids of interest. The sample nucleic acids are typically partitioned such that the nucleic acids are present in the partitions in relatively long fragments or stretches of contiguous nucleic acid molecules. Typically, these fragments of the sample nucleic acids may be longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range structural and molecular context described above.

The sample nucleic acids are also typically partitioned at a level whereby a given partition has a very low probability of including two overlapping fragments of a genomic locus. This is typically accomplished by providing the sample nucleic acid at a low input amount and/or concentration during the partitioning process. As a result, in preferred cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Published Application No. 2013-0079231 and 2013-0157870) typically only operate with a hundred to a few hundred different barcode sequences, and employ a limiting dilution process of their sample in order to be able to attribute barcodes to different cells/nucleic acids. As such, they will generally operate with far fewer than 100 cells, which would typically provide a ratio of genomes:(barcode type) on the order of 1:10, and certainly well above 1:100. The systems described herein, on the other hand, because of the high level of barcode diversity, e.g., in excess of 10,000, 100,000, 500,000, etc. diverse barcode types, can operate at genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

In further examples, the oligonucleotides included with the portions of the sample divided into the discrete partitions may comprise at least a first and second region. The first region may be a barcode region that, as between oligonucleotides within a given partition, may be substantially the same barcode sequence, but as between different partitions, may and, in most cases is a different barcode sequence. The second region may be an N-mer (either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, e.g., an exome or other targeted region. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn, as can analyses across long ranges of genomic sequence—for example, identification of sequence information across stretches of poorly characterized regions of the genome. Such information may also be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Ensemble sample preparation and sequencing methods are predisposed towards primarily identifying and characterizing the majority constituents in the sample, and are not designed to identify and characterize minority constituents, e.g., genetic material contributed by one chromosome, from a poorly characterized or highly polymorphic region of the genome, or material from one or a few cells, or fragmented tumor cell DNA molecule circulating in the bloodstream, that constitute a small percentage of the total DNA in the extracted sample. The methods described herein include selective amplification methods that increase the genetic material from these minority constituents, and the ability to retain the molecular context of this genetic material further provides genetic characterization of these constituents. The described methods and systems also provide a significant advantage for detecting populations that are present within a larger sample. As such, they are particularly useful for assessing haplotype and copy number variations—the methods disclosed herein are also useful for providing sequence information over regions of the genome that are poorly characterized or are poorly represented in a population of nucleic acid targets due to biases introduced during sample preparation.

The use of the barcoding technique disclosed herein confers the unique capability of providing individual molecular context for a given set of genetic markers, i.e., attributing a given set of genetic markers (as opposed to a single marker) to individual sample nucleic acid molecules, and through variant coordinated assembly, to provide a broader or even longer range inferred individual structural and molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

As described previously, an advantage of the methods and systems described herein is that they can achieve the desired results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, Inc. (GAIIx, NextSeq, MiSeq, HiSeq, X10), Ion Torrent division of Thermo-Fisher (Ion Proton and Ion PGM), pyrosequencing methods, as well as others.

Of particular advantage is that the methods and systems described herein utilize these short read sequencing technologies and do so with their associated low error rates and high throughputs. In particular, the methods and systems described herein achieve the desired individual molecular readlengths or context, as described above, but with individual sequencing reads, excluding mate pair extensions, that are shorter than 1000 bp, shorter than 500 bp, shorter than 300 bp, shorter than 200 bp, shorter than 150 bp or even shorter; and with sequencing error rates for such individual molecular readlengths that are less than 5%, less than 1%, less than 0.5%, less than 0.1%, less than 0.05%, less than 0.01%, less than 0.005%, or even less than 0.001%.

II. WORK FLOW OVERVIEW

In one exemplary aspect, the methods and systems described in the disclosure provide for depositing or partitioning samples into discrete partitions, where each partition maintains separation of its own contents from the contents in other partitions. As discussed in further detail herein, the samples may comprise samples derived from patients, such as cell or tissue samples, which can contain nucleic acids and, in certain situations, associated proteins as well. In specific aspects, the samples used in the methods described herein include formalin fixed paraffin embedded (FFPE) cell and tissue samples and the like, as well as any other sample types where the risk of sample degradation is high.

As used herein, the partitions refer to containers or vessels that may include a variety of different forms, e.g., wells, tubes, micro or nanowells, through holes, or the like. In preferred aspects, however, the partitions are flowable within fluid streams. These vessels may be comprised of, e.g., microcapsules or micro-vesicles that have an outer barrier surrounding an inner fluid center or core, or they may be a porous matrix that is capable of entraining and/or retaining materials within its matrix. In preferred aspect, however, these partitions may comprise droplets of aqueous fluid within a non-aqueous continuous phase, e.g., an oil phase. A variety of different vessels are described in, for example, U.S. patent application Ser. No. 13/966,150, filed Aug. 13, 2013. Likewise, emulsion systems for creating stable droplets in non-aqueous or oil continuous phases are described in detail in, e.g., Published U.S. Patent Application No. 2010-0105112. In certain cases, microfluidic channel networks are particularly suited for generating partitions as described herein. Examples of such microfluidic devices include those described in detail in Provisional U.S. Patent Application No. 61/977,804, filed Apr. 4, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of sample materials into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides. The relative amount of sample materials within any particular partition may be adjusted by controlling a variety of different parameters of the system, including, for example, the concentration of sample in the aqueous stream, the flow rate of the aqueous stream and/or the non-aqueous stream, and the like. The partitions described herein are often characterized by having extremely small volumes. For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes. In some cases, the use of low reaction volume partitions is particularly advantageous in performing reactions with very small amounts of starting reagents, e.g., input nucleic acids. Methods and systems for analyzing samples with low input nucleic acids are presented in U.S. Provisional Patent Application No. 62/017,580, filed Jun. 26, 2014, the full disclosure of which is hereby incorporated by reference in its entirety.

In situations involving samples that are subject to degradation and/or contain low concentrations of components of interest, the samples may be further processed either prior to partitioning or within the partitions to further release the nucleic acids and/or any associated proteins for further analysis. For example, nucleic acids contained in FFPE samples are generally extracted using methods known in the art. To isolate longer nucleic acid molecules, such samples may also be processed by addition of organocatalysts to remove formaldehyde adducts (see for example Karmakar et al., (2015), Nature Chemistry, DOI: 10.1038/NCHEM.2307, which is hereby incorporated by reference in its entirety and in particular for all teachings related to treatment and processing of FFPE samples.)

Once the samples are introduced into their respective partitions the sample nucleic acids within partitions may be subjected to amplification to increase the amount of nucleic acids for subsequent applications (such as sequencing methods described herein and known in the art). In certain embodiments, this amplification is conducted with a library of primers that are directed to different parts of the genomic sequence, such that the resultant amplification products represent sequences from subsections of the original nucleic acid molecules. In embodiments in which select genomic regions are of interest, this amplification may include one or more rounds of selective amplification such that regions of the genome that are of interest for targeted coverage are present in higher proportion in comparison to other regions of the genome (although, as will be appreciated, those other regions of the genome may also be amplified, but to a lesser extent, as they are not of interest for de novo coverage). In certain embodiments, the amplification provides at least 1×, 2×, 5×, 10×, 20×, 30×, 40× or 50× coverage of the whole or select regions of the genome. In further embodiments, all of the nucleic acids within a partition are amplified, but selected genomic regions are amplified in a targeted way such that at least 1-5, 2-10, 3-15, 4-20, 5-25, 6-30, 7-35, 8-40, 9-45, or 10-50 times more amplicons are produced from those selected genomic regions than from other parts of the genome.

Simultaneously with or subsequent to the amplification described above, the nucleic acids (or fragments thereof) within the partitions are provided with unique identifiers such that, upon characterization of those nucleic acids they may be attributed as having been derived from their respective origins. Accordingly, the sample nucleic acids are typically co-partitioned with the unique identifiers (e.g., barcode sequences). In particularly preferred aspects, the unique identifiers are provided in the form of oligonucleotides that comprise nucleic acid barcode sequences that may be attached to those samples. The oligonucleotides are partitioned such that as between oligonucleotides in a given partition, the nucleic acid barcode sequences contained therein are the same, but as between different partitions, the oligonucleotides can, and preferably have differing barcode sequences. In exemplary aspects, only one nucleic acid barcode sequence will be associated with a given partition, although in some cases, two or more different barcode sequences may be present.

The nucleic acid barcode sequences will typically include from 6 to about 20 or more nucleotides within the sequence of the oligonucleotides. These nucleotides may be completely contiguous, i.e., in a single stretch of adjacent nucleotides, or they may be separated into two or more separate subsequences that are separated by one or more nucleotides. Typically, separated subsequences may typically be from about 4 to about 16 nucleotides in length.

The co-partitioned oligonucleotides also typically comprise other functional sequences useful in the processing of the partitioned nucleic acids. These sequences include, e.g., targeted or random/universal amplification primer sequences for amplifying the genomic DNA from the individual nucleic acids within the partitions while attaching the associated barcode sequences, sequencing primers, hybridization or probing sequences, e.g., for identification of presence of the sequences, or for pulling down barcoded nucleic acids, or any of a number of other potential functional sequences. Again, co-partitioning of oligonucleotides and associated barcodes and other functional sequences, along with sample materials is described in, for example, U.S. Ser. Nos. 14/175,935; 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids, as well as sequencing and other characterizations of genomic material.

Briefly, in one exemplary process, beads are provided that each may include large numbers of the above described oligonucleotides releasably attached to the beads, where all of the oligonucleotides attached to a particular bead may include the same nucleic acid barcode sequence, but where a large number of diverse barcode sequences may be represented across the population of beads used. Typically, the population of beads may provide a diverse barcode sequence library that may include at least 1000 different barcode sequences, at least 10,000 different barcode sequences, at least 100,000 different barcode sequences, or in some cases, at least 1,000,000 different barcode sequences. Additionally, each bead may typically be provided with large numbers of oligonucleotide molecules attached. In particular, the number of molecules of oligonucleotides including the barcode sequence on an individual bead may be at least bout 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

The oligonucleotides may be releasable from the beads upon the application of a particular stimulus to the beads. In some cases, the stimulus may be a photo-stimulus, e.g., through cleavage of a photo-labile linkage that may release the oligonucleotides. In some cases, a thermal stimulus may be used, where elevation of the temperature of the beads environment may result in cleavage of a linkage or other release of the oligonucleotides form the beads. In some cases, a chemical stimulus may be used that cleaves a linkage of the oligonucleotides to the beads, or otherwise may result in release of the oligonucleotides from the beads.

In accordance with the methods and systems described herein, the beads including the attached oligonucleotides may be co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 3:
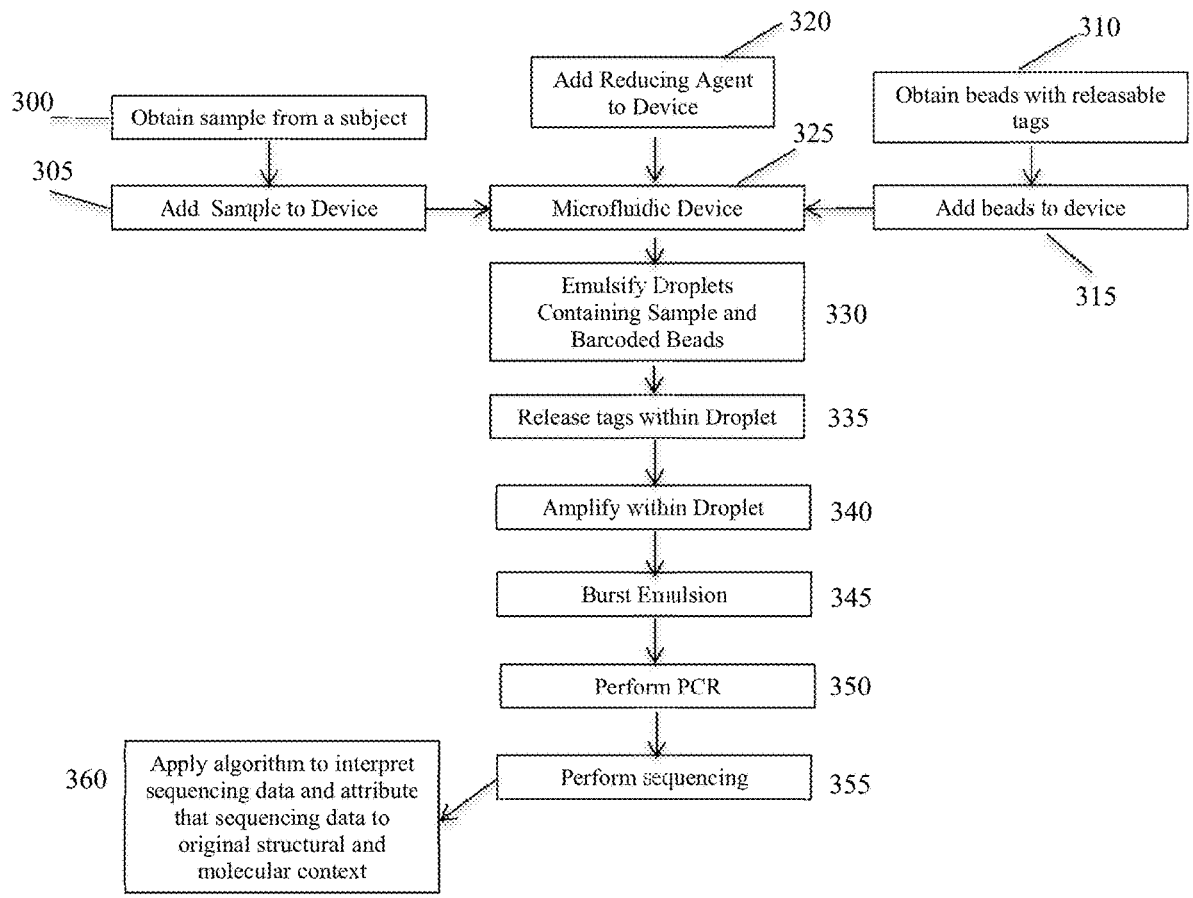
FIG. 3 illustrates a typical workflow for performing an assay to detect sequence information, using the methods and compositions disclosed herein.

FIG. 3 illustrates one particular example method for barcoding and subsequently sequencing a sample nucleic acid. First, a sample comprising nucleic acid may be obtained from a source, 300, and a set of barcoded beads may also be obtained, 310. The beads are preferably linked to oligonucleotides containing one or more barcode sequences, as well as a primer, such as a random N-mer or other primer. Preferably, the barcode sequences are releasable from the barcoded beads, e.g., through cleavage of a linkage between the barcode and the bead or through degradation of the underlying bead to release the barcode, or a combination of the two. For example, in certain preferred aspects, the barcoded beads can be degraded or dissolved by an agent, such as a reducing agent to release the barcode sequences. In this example, a low quantity of the sample comprising nucleic acid, 305, barcoded beads, 315, and optionally other reagents, e.g., a reducing agent, 320, are combined and subject to partitioning. By way of example, such partitioning may involve introducing the components to a droplet generation system, such as a microfluidic device, 325. With the aid of the microfluidic device 325, a water-in-oil emulsion 330 may be formed, wherein the emulsion contains aqueous droplets that contain sample nucleic acid, 305, reducing agent, 320, and barcoded beads, 315. The reducing agent may dissolve or degrade the barcoded beads, thereby releasing the oligonucleotides with the barcodes and random N-mers from the beads within the droplets, 335. The random N-mers may then prime different regions of the sample nucleic acid, resulting in amplified copies of the sample after amplification, wherein each copy is tagged with a barcode sequence, 340. Preferably, each droplet contains a set of oligonucleotides that contain identical barcode sequences and different random N-mer sequences. Subsequently, the emulsion is broken, 345 and additional sequences (e.g., sequences that aid in particular sequencing methods, additional barcodes, etc.) may be added, via, for example, amplification methods, 350 (e.g., PCR). Sequencing may then be performed, 355, and an algorithm applied to interpret the sequencing data, 360. Sequencing algorithms are generally capable, for example, of performing analysis of barcodes to align sequencing reads and/or identify the sample from which a particular sequence read belongs. In addition, and as is described herein, these algorithms may also further be used to attribute the sequences of the copies to their originating molecular context.

As will be appreciated, prior to or simultaneously with tagging with the barcode sequence 340, the samples can be amplified in accordance with any of the methods described herein to provide coverage of the whole genome or of selected regions of the genome. For embodiments in which targeted coverage is desired, the targeted amplification generally results in a larger population of amplicons representing sequences of the nucleic acids (or portions of thereof) in a partition containing those selected regions of the genome as compared to amplicons from other regions of the genome. As a result, there will be a larger number of the amplified copies containing barcode sequence 340 within a partition from the selected regions of the genome than from other regions of the genome. In embodiments in which whole genome amplification is desired, the amplification may be conducted using primer libraries designed to minimize amplification biases and provide a robust level of coverage across the entire genome.

Figure 4:
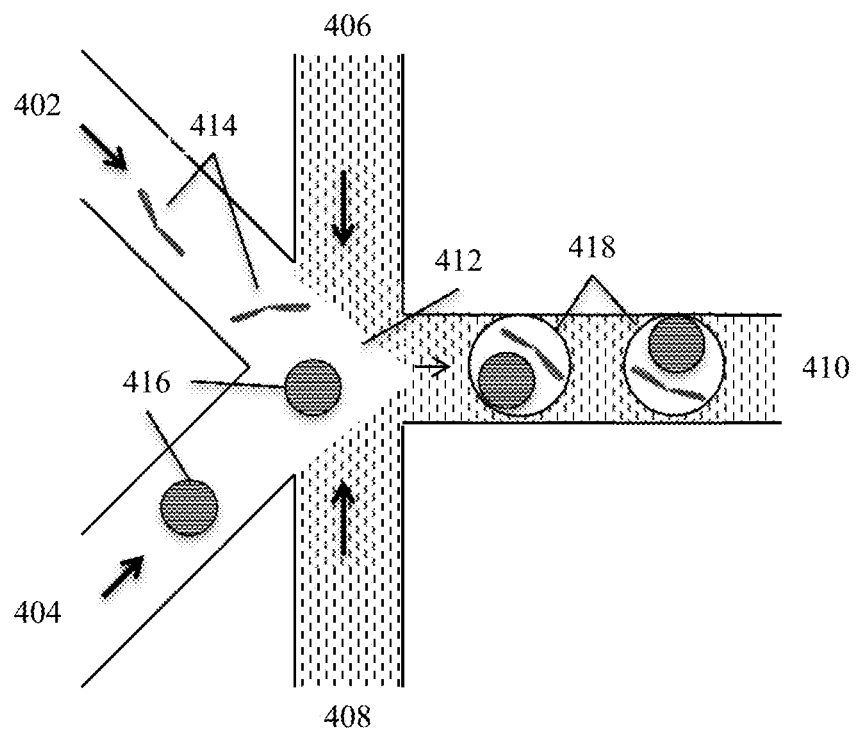
FIG. 4 provides a schematic illustration of a process for combining a nucleic acid sample with beads and partitioning the nucleic acids and beads into discrete droplets.

As noted above, while single occupancy may be the most desired state, it will be appreciated that multiply occupied partitions or unoccupied partitions may often be present. An example of a microfluidic channel structure for co-partitioning samples and beads comprising barcode oligonucleotides is schematically illustrated in FIG. 4. As shown, channel segments 402, 404, 406, 408 and 410 are provided in fluid communication at channel junction 412. An aqueous stream comprising the individual samples 414 is flowed through channel segment 402 toward channel junction 412. As described elsewhere herein, these samples may be suspended within an aqueous fluid prior to the partitioning process.

Concurrently, an aqueous stream comprising the barcode carrying beads 416 is flowed through channel segment 404 toward channel junction 412. A non-aqueous partitioning fluid is introduced into channel junction 412 from each of side channels 406 and 408, and the combined streams are flowed into outlet channel 410. Within channel junction 412, the two combined aqueous streams from channel segments 402 and 404 are combined, and partitioned into droplets 418, that include co-partitioned samples 414 and beads 416. As noted previously, by controlling the flow characteristics of each of the fluids combining at channel junction 412, as well as controlling the geometry of the channel junction, one can optimize the combination and partitioning to achieve a desired occupancy level of beads, samples or both, within the partitions 418 that are generated.

As will be appreciated, a number of other reagents may be co-partitioned along with the samples and beads, including, for example, chemical stimuli, nucleic acid extension, transcription, and/or amplification reagents such as polymerases, reverse transcriptases, nucleoside triphosphates or NTP analogues, primer sequences and additional cofactors such as divalent metal ions used in such reactions, ligation reaction reagents, such as ligase enzymes and ligation sequences, dyes, labels, or other tagging reagents. The primer sequences may include random primer sequences or targeted PCR primers directed to amplifying selected regions of the genome or a combination thereof.

Once co-partitioned, the oligonucleotides disposed upon the bead may be used to barcode and amplify the partitioned samples. A particularly elegant process for use of these barcode oligonucleotides in amplifying and barcoding samples is described in detail in U.S. Ser. Nos. 14/175,935; 14/316,383; 14/316,398; 14/316,416; 14/316,431; 14/316,447; and 14/316,463, the full disclosures of which are hereby incorporated by reference in their entireties. Briefly, in one aspect, the oligonucleotides present on the beads that are co-partitioned with the samples and released from their beads into the partition with the samples. The oligonucleotides typically include, along with the barcode sequence, a primer sequence at its 5' end. The primer sequence may be random or structured. Random primer sequences are generally intended to randomly prime numerous different regions of the samples. Structured primer sequences can include a range of different structures including defined sequences targeted to prime upstream of a specific targeted region of the sample as well as primers that have some sort of partially defined structure, including without limitation primers containing a percentage of specific bases (such as a percentage of GC N-mers), primers containing partially or wholly degenerate sequences, and/or primers containing sequences that are partially random and partially structured in accordance with any of the description herein. As will be appreciated, any one or more of the above types of random and structured primers may be included in oligonucleotides in any combination.

Figure 5:
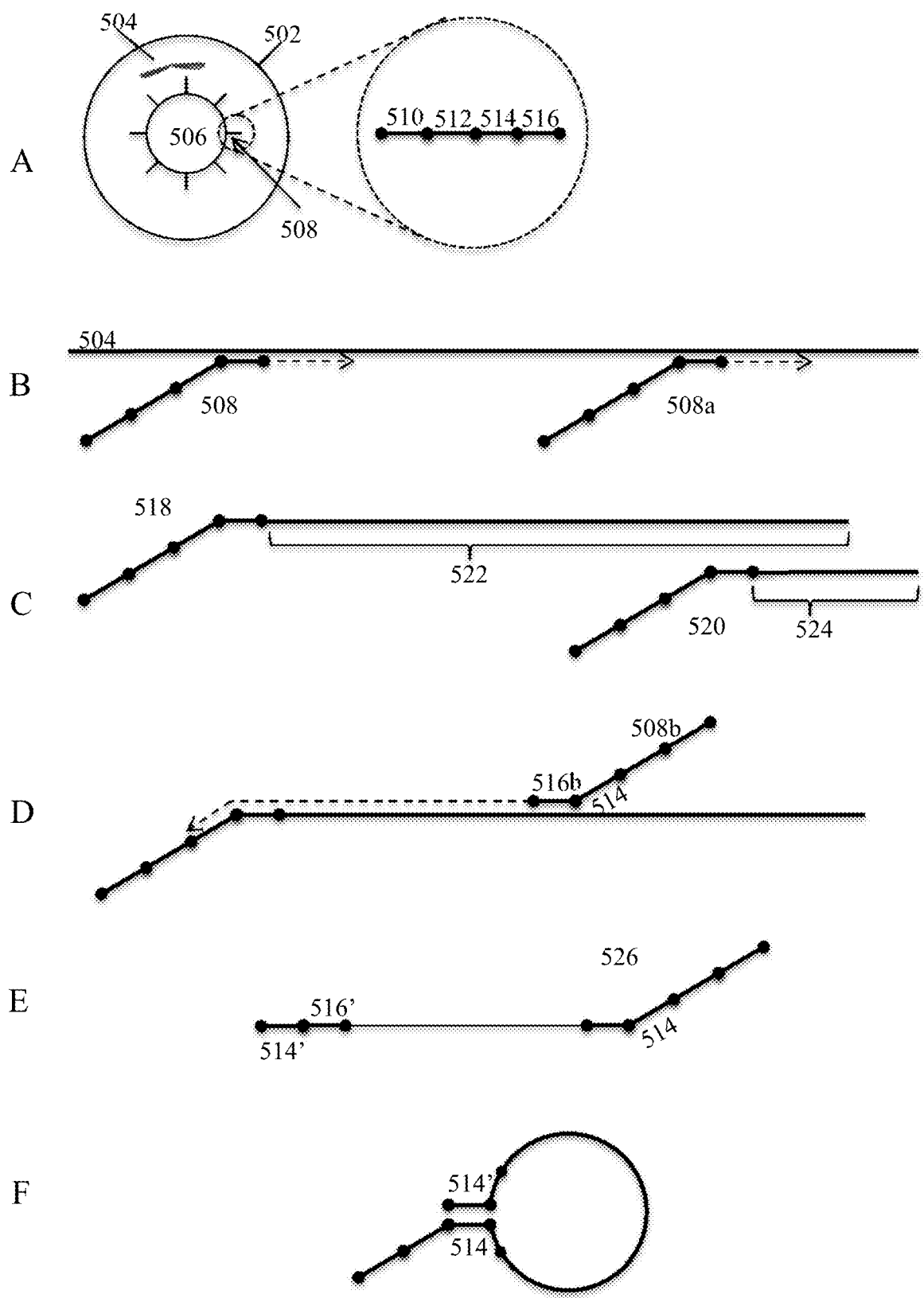
FIG. 5 provides a schematic illustration of a process for barcoding and amplification of chromosomal nucleic acid fragments.

Once released, the primer portion of the oligonucleotide can anneal to a complementary region of the sample. Extension reaction reagents, e.g., DNA polymerase, nucleoside triphosphates, co-factors (e.g., Mg2+ or Mn2+ etc.), that are also co-partitioned with the samples and beads, then extend the primer sequence using the sample as a template, to produce a complementary fragment to the strand of the template to which the primer annealed, with complementary fragment includes the oligonucleotide and its associated barcode sequence. Annealing and extension of multiple primers to different portions of the sample may result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure, which reduces the ability of the molecule to be the basis for producing further iterative copies. A schematic illustration of one example of this is shown in FIG. 5.

As the figure shows, oligonucleotides that include a barcode sequence are co-partitioned in, e.g., a droplet 502 in an emulsion, along with a sample nucleic acid 504. As noted elsewhere herein, the oligonucleotides 508 may be provided on a bead 506 that is co-partitioned with the sample nucleic acid 504, which oligonucleotides are preferably releasable from the bead 506, as shown in panel A. The oligonucleotides 508 include a barcode sequence 512, in addition to one or more functional sequences, e.g., sequences 510, 514 and 516. For example, oligonucleotide 508 is shown as comprising barcode sequence 512, as well as sequence 510 that may function as an attachment or immobilization sequence for a given sequencing system, e.g., a P5 sequence used for attachment in flow cells of an Illumina Hiseq or Miseq system. As shown, the oligonucleotides also include a primer sequence 516, which may include a random or targeted N-mer for priming replication of portions of the sample nucleic acid 504. Also included within oligonucleotide 508 is a sequence 514 which may provide a sequencing priming region, such as a "read1" or R1 priming region, that is used to prime polymerase mediated, template directed sequencing by synthesis reactions in sequencing systems. In many cases, the barcode sequence 512, immobilization sequence 510 and R1 sequence 514 may be common to all of the oligonucleotides attached to a given bead. The primer sequence 516 may vary for random N-mer primers, or may be common to the oligonucleotides on a given bead for certain targeted applications.

Based upon the presence of primer sequence 516, the oligonucleotides are able to prime the sample nucleic acid as shown in panel B, which allows for extension of the oligonucleotides 508 and 508a using polymerase enzymes and other extension reagents also co-portioned with the bead 506 and sample nucleic acid 504. As shown in panel C, following extension of the oligonucleotides that, for random N-mer primers, would anneal to multiple different regions of the sample nucleic acid 504; multiple overlapping complements or fragments of the nucleic acid are created, e.g., fragments 518 and 520. Although including sequence portions that are complementary to portions of sample nucleic acid, e.g., sequences 522 and 524, these constructs are generally referred to herein as comprising fragments of the sample nucleic acid 504, having the attached barcode sequences. As will be appreciated, the replicated portions of the template sequences as described above are often referred to herein as "fragments" of that template sequence. Notwithstanding the foregoing, however, the term "fragment" encompasses any representation of a portion of the originating nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In preferred aspects, however, fragments of a template or sample nucleic acid sequence will denote replicated portions of the underlying sequence or complements thereof.

The barcoded nucleic acid fragments may then be subjected to characterization, e.g., through sequence analysis, or they may be further amplified in the process, as shown in panel D. For example, additional oligonucleotides, e.g., oligonucleotide 508b, also released from bead 506, may prime the fragments 518 and 520. In particular, again, based upon the presence of the random N-mer primer 516b in oligonucleotide 508b (which in many cases will be different from other random N-mers in a given partition, e.g., primer sequence 516), the oligonucleotide anneals with the fragment 518, and is extended to create a complement 526 to at least a portion of fragment 518 which includes sequence 528, that comprises a duplicate of a portion of the sample nucleic acid sequence. Extension of the oligonucleotide 508b continues until it has replicated through the oligonucleotide portion 508 of fragment 518. As noted elsewhere herein, and as illustrated in panel D, the oligonucleotides may be configured to prompt a stop in the replication by the polymerase at a desired point, e.g., after replicating through sequences 516 and 514 of oligonucleotide 508 that is included within fragment 518. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 512 to prevent a non-uracil tolerant polymerase to cease replication of that region. As a result a fragment 526 is created that includes the full-length oligonucleotide 508b at one end, including the barcode sequence 512, the attachment sequence 510, the R1 primer region 514, and the random N-mer sequence 516b. At the other end of the sequence will be included the complement 516' to the random N-mer of the first oligonucleotide 508, as well as a complement to all or a portion of the R1 sequence, shown as sequence 514'. The R1 sequence 514 and its complement 514' are then able to hybridize together to form a partial hairpin structure 528. As will be appreciated because the random N-mers differ among different oligonucleotides, these sequences and their complements would not be expected to participate in hairpin formation, e.g., sequence 516', which is the complement to random N-mer 516, would not be expected to be complementary to random N-mer sequence 516b. This would not be the case for other applications, e.g., targeted primers, where the N-mers would be common among oligonucleotides within a given partition. By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 526.

Figure 6:
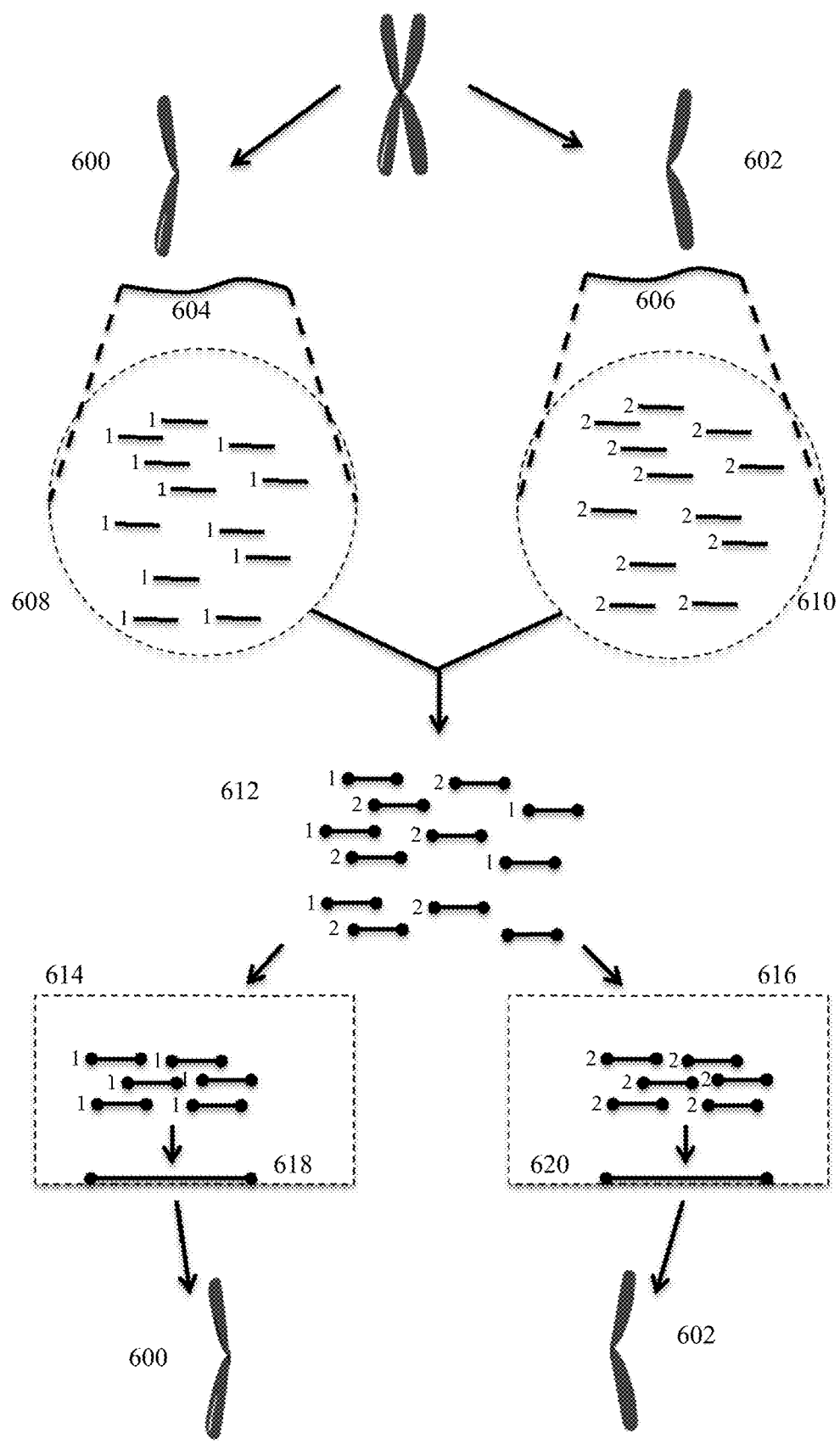
FIG. 6 provides a schematic illustration of the use of barcoding of nucleic acid fragments in attributing sequence data to their originating source nucleic acid molecule.

All of the fragments from multiple different partitions may then be pooled for sequencing on high throughput sequencers as described herein. Because each fragment is coded as to its partition of origin, the sequence of that fragment may be attributed back to its origin based upon the presence of the barcode. This is schematically illustrated in FIG. 6. As shown in one example, a nucleic acid 604 originated from a first source 600 (e.g., individual chromosome, strand of nucleic acid, etc.) and a nucleic acid 606 derived from a different chromosome 602 or strand of nucleic acid are each partitioned along with their own sets of barcode oligonucleotides as described above.

Within each partition, each nucleic acid 604 and 606 is then processed to separately provide overlapping set of second fragments of the first fragment(s), e.g., second fragment sets 608 and 610. This processing also provides the second fragments with a barcode sequence that is the same for each of the second fragments derived from a particular first fragment. As shown, the barcode sequence for second fragment set 608 is denoted by "1" while the barcode sequence for fragment set 610 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 608 and 610, may then be pooled for sequencing using, for example, sequence by synthesis technologies available from Illumina or Ion Torrent division of Thermo Fisher, Inc., and the like. Once sequenced, the sequence reads from the pooled fragments 612 can be attributed to their respective fragment set, e.g., as shown in aggregated reads 614 and 616, at least in part based upon the included barcodes, and optionally, and preferably, in part based upon the sequence of the fragment itself. In addition, the sequence reads can be attributed to the structural context of the relative position of the nucleic acid from which those reads are derived in relation to other nucleic acid molecules that were in close spatial proximity within the original sample. The attributed sequence reads for each fragment set are then assembled to provide the assembled sequence for each sample fragment, e.g., sequences 618 and 620, which in turn, may be further attributed back to their respective original chromosomes or source nucleic acid molecules (600 and 602). Methods and systems for assembling genomic sequences are described in, for example, U.S. patent application Ser. No. 14/752,773, filed Jun. 26, 2015, the full disclosure of which is hereby incorporated by reference in its entirety and in particular for all teachings related to assembly of genomic sequences.

III. METHODS AND COMPOSITIONS FOR RETAINING STRUCTURAL CONTEXT

This disclosure provides methods, compositions and systems for characterization of genetic material. In general, the methods, compositions and systems described herein provide methods of analyzing components of a sample while retaining information on the structural as well as molecular context of those components as they were originally in the sample. In other words, the description herein relation generally to spatial detection of nucleic acids in a sample, including tissue samples that have been or will be fixed using methods known in the art, such as formalin fixed paraffin embedded samples. As will be appreciated, any of the methods described in this section can be combined with any of the methods described above in the sections entitled "Overview" and "Workflow Overview" as well as with the nucleic acid sequencing methods described in subsequent sections of this specification.

In general, the methods disclosed herein relate to determining and/or analyzing nucleic acids in a sample, including genomes, particularly the global genome, of a sample. The methods described herein provide the ability to quantitatively or qualitatively analyze the distribution, location or expression of nucleic acid sequences (including genomic sequences) in a sample wherein the spatial context within the sample is retained. The methods disclosed herein provide an advantage over conventional methods of geographic encoding of nucleic acids in a sample, because information on structural context is retained in a high throughput processing method without requiring identification of particular molecular targets (such as specific genes or other nucleic acid sequences) prior to processing the sample for sequence reads. In addition, low amounts of nucleic acid are needed, which is particularly advantageous in samples such as FFPE samples in which the input nucleic acids, particularly DNA, are often fragmented or present in low concentrations.

Although much of the discussion herein is in terms of the analysis of nucleic acids, it will be appreciated that the methods and systems discussed herein can be adapted to apply to other components of a sample, including proteins and other molecules.

As discussed above, maintaining structural context, also referred to herein as maintaining geographical context and encoding geography, means using methods that allow for obtaining multiple sequence reads or multiple portions of sequence reads that can be attributed to the original three-dimensional relative location of those sequence reads within a sample. In other words, the sequence reads can be associated with a relative location within the sample with respect to neighboring nucleic acids (and in some situations associated proteins) in that sample. This spatial information is available even if those neighboring nucleic acids are not physically located within the linear sequence of a single originating nucleic acid molecule.

In general, the methods described herein include analyses in which a sample containing nucleic acids is provided, where the nucleic acids contain three dimensional structures. Portions of the sample are separated into discrete partitions such that portions of the nucleic acid three dimensional structures are also separated into the discrete partitions—nucleic acid sequences that are in spatial proximity to each other will tend to be separated into the same partition, thus retaining the three-dimensional information of that spatial proximity even when later-obtained sequence reads are from sequences that were not originally on the same individual originating nucleic acid molecule. Referring to FIG. 1: if sample 101, containing nucleic acid molecules 102 and 103 and 106, is separated into discrete partitions such that subsets of the sample are allocated into different discrete partitions, it is more likely that nucleic acid molecules 102 and 103 will be placed in the same partition with each other than with nucleic acid molecule 106, because of the physical distance between nucleic acid molecule 106 and 102 and 103. As such, nucleic acid molecules within the same discrete partitions are those that were in spatial proximity to each other in the original sample. Sequence information obtained from nucleic acids within the discrete partitions thus provides a way to analyze the nucleic acids, for example through nucleic acid sequencing, and attribute those sequence reads back to the structural context of the originating nucleic acid molecules.

In some examples, a library of tags is applied to the sample for spatial or geographic encoding of the sample. In certain embodiments, the tags are oligonucleotide tags (which can include "oligonucleotide barcodes" and "DNA barcodes"), but as will be appreciated, any type of tag that is capable of being added into a sample can be used, including without limitation particles, beads, dyes, molecular inversion probes (MIPs), and the like. The library of tags can be applied to the sample through simple diffusion, or through active processes, such as cellular processes within tissue culture or cell culture samples. Cellular transport processes include without limitation osmosis, facilitated diffusion through the involvement of cell transport proteins, passive transport, and active transport through the involvement of cell transport proteins and input of energy from molecules such as ATP. In general, the tags are applied such that different spatial/geographic locations within the sample receive different tags and/or a different concentration of tags. Any further processing of the sample and analysis of the nucleic acids within the sample can be attributed to a particular spatial context through identification of the tags. For example, referring to FIG. 1, addition of a library of tags to sample 101 would result in nucleic acids 102 and 103 having spatial proximity to a different portion or concentration of the library of tags than nucleic acid 106. Any further processing of the sample in accordance to the workflows described herein would then result in nucleic acids 102 and 103 being associated with the same portion/concentration of tags, and thus identification of those tags would indicate that nucleic acids 102 and 103 were in spatial proximity to each other in the original sample 101. Identification of nucleic acid 106 with a different portion/concentration of tags would show that nucleic acid 106 was at a different spatial location than nucleic acids 102 and 103 in the original sample.

In further examples, partition-specific barcodes are also employed, such that any sequence reads obtained can be attributed back to the partition in which the originating nucleic acid molecules were located. As discussed above, associating sequence reads to a particular partition identifies nucleic acid molecules that were in spatial proximity to each other in the geography of the original sample. Further use of workflows, such as those pictured in FIG. 2, also provides information on the molecular context of the sequence reads, such that individual sequence reads can be attributed to the individual nucleic acid molecules from which they originated.

To enable tagging of samples, the samples may be processed using any methods known in the art to allow application of exogenous molecules such as oligonucleotide tags or other labels. For example, in embodiments in which FFPE samples are used, tags can be applied to the samples by heating the sample to allow embedding of the tags into the sample, and then the sample could be cooled and further processed in accordance with any of the methods described herein, including division into discrete partitions and further analysis to identify sequences of nucleic acids in the sample and the tags that are also in close spatial proximity to those sequence reads, thus retaining structural context of those sequence reads. Other sample processing methods include tissue processing methods that remove extracellular matrix and/or other structural impediments while retaining molecular and protein elements. Such methods include in some non-limiting examples the CLARITY method as well as the use of other tissue clearing and labeling methods, including those described for example in Tomer et al., VOL. 9 NO. 7, 2014, Nature Protocols; Kebschull et al., Neuron, Volume 91 Issue 5, 7 Sep. 2016, Pages 975-987; Chung, K. et al. Structural and molecular interrogation of intact biological systems. Nature 497, 332-337 (2013); Susaki, E. A. et al. Whole-brain imaging with single-cell resolution using chemical cocktails and computational analysis. Cell 157, 726-739 (2014); and Lee et al., ACT-PRESTO: Rapid and consistent tissue clearing and labeling method for 3-dimensional (3D) imaging, Scientific Reports, 2016/01/11/online; Vol. 6, p. 18631, each of which is hereby incorporated by reference in its entirety for all purposes, and in particular for any teachings related to processing samples for use in structural and molecular interrogation methods.

In certain embodiments, the methods described herein are used in combination with imaging techniques to identify spatial locations of the tags within the sample, particularly for samples that are immobilized on slides, such as FFPE samples. Such imaging techniques may allow correlation of sequence reads to particular locations on the slides, which allows correlation with other pathological/imaging studies that may have been conducted with those samples. For example, imaging techniques may be used to provide a preliminary identification of a pathology. The sequencing techniques described herein that further provide sequence reads while maintaining structural context could be combined with such imaging analysis to correlate sequence reads with structural context to corroborate or provide further information on that preliminary identification of the pathology. In addition, the imaging techniques may be used in combination with tags with optical properties, such that particular tags are associated with particular regions of the imaged sample. Sequence reads that are correlated with those identified tags could then be further correlated with regions of the imaged sample by virtue of their location with those tags. However, it will be appreciated that the methods described herein are independent of any such imaging techniques, and the ability to retain structural context is not dependent on using an imaging technique for determining spatial information of nucleic acids in the sample.

In one exemplary aspect, gradients of oligonucleotides are generated in a sample to provide a coordinate system that can be decoded through later processing through sequencing. Such a gradient will allow tagging of cells and/or nucleic acids in the sample with an oligonucleotide or oligonucleotide concentration, which can be mapped to a physical location within the original sample. This coordinate system can be developed by allowing a library of oligonucleotides to diffuse into a sample and/or by injecting oligonucleotides into particular regions of the sample. When using diffusion, standard calculations of diffusion kinetics will provide a correlation between the concentration of the oligonucleotide tags and its spatial location in the original sample. Thus, any other nucleic acids identified with that concentration of oligonucleotide tags can in turn be correlated to a particular geographic region of the sample.

In further exemplary embodiments, the methods include processes for analyzing nucleic acids while maintaining structural context in which a library of tags is applied to a sample such that different geographical regions of the sample receive different tags. Portions of the sample, which now contain their original nucleic acids as well as the added tags, are then separated into discrete partitions, such that portions of the library of tags and portions of the nucleic acids that are close to each other in geographic location within the sample end up in the same discrete partition. Sequencing processes, such as those described in detail herein, are used to provide sequence reads of nucleic acids in the discrete partitions. The tags can also be identified before, after or simultaneously with those sequencing processes. The correlation of sequence reads to particular tags (or concentrations of tags in embodiments in which concentration gradients of tags are used) thereby helps to provide the spatial context of the sequence reads. As discussed above, embodiments in which the tags used for spatial encoding are used in conjunction with partition-specific barcoding further provide structural and molecular context for the sequence reads.

IV. APPLICATIONS OF METHODS AND SYSTEMS TO NUCLEIC ACID SEQUENCING

The methods, compositions, and systems described herein are particularly amenable for use in nucleic acid sequencing technologies. Such sequencing technologies can include any technologies known in the art, including short-read and long-read sequencing technologies. In certain aspects, the methods, compositions and systems described herein are used in short read, high accuracy sequencing technologies.

In general, the methods and systems described herein accomplish genomic sequencing using methods that have the advantages of the extremely low sequencing error rates and high throughput of short read sequencing technologies. As described previously, an advantage of the methods and systems described herein is that they can achieve the desired results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, Inc. (GAIIx, NextSeq, MiSeq, HiSeq, X10), Ion Torrent division of Thermo-Fisher (Ion Proton and Ion PGM), pyrosequencing methods, as well as others.

Of particular advantage is that the methods and systems described herein utilize these short read sequencing technologies and do so with their associated low error rates. In particular, the methods and systems described herein achieve the desired individual molecular readlengths or context, as described above, but with individual sequencing reads, excluding mate pair extensions, that are shorter than 1000 bp, shorter than 500 bp, shorter than 300 bp, shorter than 200 bp, shorter than 150 bp or even shorter; and with sequencing error rates for such individual molecular read-lengths that are less than 5%, less than 1%, less than 0.5%, less than 0.1%, less than 0.05%, less than 0.01%, less than 0.005%, or even less than 0.001%.

Methods of processing and sequencing nucleic acids in accordance with the methods and systems described in the present application are also described in further detail in U.S. Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material.

In some embodiments, the methods and systems described herein for obtaining sequence information while retaining both structural and molecular context are used for whole genome sequencing. In some embodiments, the methods described herein are used for sequencing of targeted regions of the genome. In further embodiments, the sequencing methods described herein include a combination of deep coverage of the selected regions with lower level linked reads across longer ranges of the genome. As will be appreciated, this combination of de novo and re-sequencing provides an efficient way to sequence an entire genome and/or large portions of a genome. Targeted coverage of poorly characterized and/or highly polymorphic regions further provides the amount of nucleic acid material necessary for de novo sequence assembly, whereas linked genomic sequencing over other regions of the genome maintains high throughput sequencing of the remainder of the genome. The methods and compositions described herein are amenable to allowing for this combination of de novo and linked read sequencing, because the same sequencing platform can be used for both types of coverage. The population of nucleic acids and/or nucleic acid fragments that are sequenced in accordance with the methods described herein can contain sequences from both the genomic regions for de novo sequencing and the genomic regions for re-sequencing.

In specific instances, methods described herein include a step in which the whole or selected regions of the genome are amplified prior to sequencing. This amplification, which is generally conducted using methods known in the art (including without limitation PCR amplification) provides at least 1×, 2×, 3×, 4×, 5×, 6×, 7×, 8×, 9×, 10×, 11×, 12×, 13×, 14×, 15×, 16×, 17×, 18×, 19×, or 20× coverage of the whole or selected regions of the genome. In further embodiments, the amplification provides at least 1×-30×, 2×-25×, 3×-20×, 4×-15×, or 5×-10× coverage of the whole or selected regions of the genome.

Amplification for coverage of the whole genome and/or select targeted regions of the genome generally conducted through extension of primers complementary to sequences within or near the selected regions of the genome. In some cases, a library of primers is used that is designed to tile across genomic regions of interest—in other words, the library of primer is designed to amplify regions at specific distances along the genome, whether this is across selected regions or across the whole genome. In some instances, the selective amplification utilizes primers that are complementary to every 10, 15, 20, 25, 50, 100, 200, 250, 500, 750, 1000, or 10000 bases along the selected regions of the genome. In still further examples, the tiled library of primers is designed to capture a mixture of distances—that mixture can be a random mixture of distances or intelligently designed such that specific portions or percentages of the selected regions are amplified by different primer pairs. In further embodiments, the primer pairs are designed such that each pair amplifies about 1-5%, 2-10%, 3-15%, 4-20%, 5-25%, 6-30%, 7-35%, 8-40%, 9-45%, or 10-50% of any contiguous region of a selected portion of the genome.

In certain embodiments and in accordance with any of the description above, the amplification occurs across a region of the genome that is at least 3 megabasepairs long (Mb). In further embodiments, a selected region of the genome is selectively amplified in accordance with any of the methods described herein, and that selected region is at least 3.5, 4, 4.5, 5, 5.5, 6, 6.5, 7, 7.5, 8, 8.5, 9, 9.5, or 10 Mb long. In yet further embodiments, the selected region of the genome is about 2-20, 3-18, 4-16, 5-14, 6-12, or 7-10 Mb in length. Amplification may occur across these regions using a single primer pair complementary to sequences at the ends or near the ends of these regions. In other embodiments, amplification is conducted with a library of primer pairs that are tiled across the length of the region, such that regular segments, random segments, or some combination of different segment distances along the region are amplified, with the extent of coverage in accordance with the description above.

In some embodiments, the primers used in selective amplification of selected regions of the genome contain uracils so that the primers themselves are not amplified.

Regardless of the sequencing platform used, in general and in accordance with any of the methods described herein, sequencing of nucleic acids is typically carried out in a manner that preserves the structural and molecular context of sequence reads or portions of sequence reads. By that is meant that multiple sequence reads or multiple portions of sequence reads may be attributable to the relative spatial location within the original sample with respect to other nucleic acids (structural context) and/or to the location within the linear sequence of a single originating molecule of a nucleic acid (molecular context).

As will be appreciated, while the single originating molecule of a nucleic acid may be of any of a variety of lengths, in preferred aspects, it will be a relatively long molecule, allowing for preservation of long range molecular context. In particular, the single originating molecule is preferably substantially longer than the typical short read sequence length, e.g., longer than 200 bases, and is often at least 1000 bases or longer, 5000 bases or longer, 10,000 bases or longer, 20,000 bases or longer, 30,000 bases or longer, 40,000 bases or longer, 50,000 bases or longer, 60,000 bases or longer, 70,000 bases or longer, 80,000 bases or longer, 90,000 bases or longer, or 100,000 bases or longer, and in some cases 1 megabase or longer.

Generally, methods of the invention include steps as illustrated in FIG. 2, which provides a schematic overview of methods of the invention discussed in further detail herein. As will be appreciated, the method outlined in FIG. 2 is an exemplary embodiment that may be altered or modified as needed and as described herein.

As shown in FIG. 2, the methods described herein will in most examples include a step in which samples are partitioned (202). Prior to that partitioning step, there may be an optional step (201) in which nucleic acids in the sample are linked to attach sequence regions that are in close spatial proximity to each other. Generally, each partition containing nucleic acids from genomic regions of interest will undergo some kind of fragmentation process and the original molecular context of the fragments will generally be retained (203), usually by barcoding the fragments that are specific to the partition in which they are contained. Each partition may in some examples include more than one nucleic acid, and will in some instances contain several hundred nucleic acid molecules—in situations in which multiple nucleic acids are within a partition, any particular locus of the genome will generally be represented by a single individual nucleic acid prior to barcoding. As discussed above, barcoded fragments of step 203 can be generated using any methods known in the art—in some examples, oligonucleotides are the samples within the distinct partitions. Such oligonucleotides may comprise random sequences intended to randomly prime numerous different regions of the samples, or they may comprise a specific primer sequence targeted to prime upstream of a targeted region of the sample. In further examples, these oligonucleotides also contain a barcode sequence, such that the replication process also barcodes the resultant replicated fragment of the original sample nucleic acid. Extension reaction reagents, e.g., DNA polymerase, nucleoside triphosphates, co-factors (e.g., $Mg^{2+}$ or $Mn^{2+}$ etc.), that are also contained in the partitions, then extend the primer sequence using the sample as a template, to produce a complementary fragment to the strand of the template to which the primer annealed, and the complementary fragment includes the oligonucleotide and its associated barcode sequence. Annealing and extension of multiple primers to different portions of the sample can result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In further examples, this replication process is configured such that when the first complement is duplicated, it produces two complementary sequences at or near its termini to allow the formation of a hairpin structure or partial hairpin structure, which reduces the ability of the molecule to be the basis for producing further iterative copies.

Returning to the method exemplified in FIG. 2, once the partition-specific barcodes are attached to the copied fragments, the barcoded fragments can optionally then be pooled (204). The pooled fragments are then sequenced (205) and the sequences of the fragments are attributed to their originating molecular context (206), such that the targeted regions of interest are both identified and also linked with that originating molecular context. An advantage of the methods and systems described herein is that attaching a partition- or sample-specific barcode to the copied fragments prior to enriching the fragments for targeted genomic regions preserves the original molecular context of those targeted regions, allowing them to be attributed to their original partition and thus their originating sample nucleic acid.

In addition to the above workflow, targeted genomic regions may be further enriched, isolated or separated, i.e., "pulled down," for further analysis, particularly sequencing, using methods that include both chip-based and solution-based capture methods. Such methods utilize probes that are complementary to the genomic regions of interest or to regions near or adjacent to the genomic regions of interest. For example, in hybrid (or chip-based) capture, microarrays containing capture probes (usually single-stranded oligonucleotides) with sequences that taken together cover the region of interest are fixed to a surface. Genomic DNA is fragmented and may further undergo processing such as end-repair to produce blunt ends and/or addition of additional features such as universal priming sequences. These fragments are hybridized to the probes on the microarray. Unhybridized fragments are washed away and the desired fragments are eluted or otherwise processed on the surface for sequencing or other analysis, and thus the population of fragments remaining on the surface is enriched for fragments containing the targeted regions of interest (e.g., the regions comprising the sequences complementary to those contained in the capture probes). The enriched population of fragments may further be amplified using any amplification technologies known in the art. Exemplary methods for such targeted pull down enrichment methods are described in U.S. Ser. No. 62/072,164, filed on Oct. 29, 2014, which is hereby incorporated by reference in its entirety for all purposes and in particular for all teachings related to targeted pull down enrichment methods and sequencing methods, including all written description, figures and examples.

In some examples, rather than whole genome sequencing, it is desirable to focus on selected regions of the genome. The methods described herein are particularly amenable to such analyses, because the ability to target subsets of the genome, even when those subsets are at large linear distances but potentially in near proximity in the three-dimensional context of the original sample, is an advantageous feature of these methods. In some aspects, methods for coverage of selected regions of the genome include methods in which the discrete partitions containing nucleic acid molecules and/or fragments thereof from those selected regions are themselves sorted for further processing. As will be appreciated, this sorting of the discrete partitions may take place in any combination with other methods of selective amplification and/or targeted pull-down of genomic regions of interest described herein, in particular in any combination with the steps of the work flow described above.

In general, methods of sorting of the discrete partitions includes steps in which partitions containing at least a portion of the one or more selected portions of the genome are separated from partitions that do not contain any sequences from those portions of the genome. These methods include the steps of providing a population enriched for sequences of the fragments comprising at least a portion of the one or more selected portions of the genome within the discrete partitions containing sequences from those portions of the genome. Such enrichment is generally accomplished through the use of directed PCR amplification of the fragments within the discrete partitions that include at least a portion of the one or more selected portions of the genome to produce a population. This directed PCR amplification thus produces amplicons comprising at least a portion of the one or more selected portions of the genome. In certain embodiments, these amplicons are attached to a detectable label, which in some non-limiting embodiments may include a fluorescent molecule. In general, such attachment occurs such that only those amplicons generated from the fragments containing the one or more selected portions of the genome are attached to the detectable label. In some embodiments, the attachment of the detectable labels occurs during the selective amplification of the one or more selected portions of the genome. Such detectable labels may in further embodiments include without limitation fluorescent labels, electrochemical labels, magnetic beads, and nanoparticles. This attachment of the detectable label can be accomplished using methods known in the art. In yet further embodiments, discrete partitions containing fragments comprising at least a portion of the one or more selected portions of the genome are sorted based on signals emitted from the detectable labels attached to the amplicons within those partitions.

In further embodiments, the steps of sorting discrete partitions containing selected portions of the genome from those that do not contain such sequences include the steps of (a) providing starting genomic material; (b) distributing individual nucleic acid molecules from the starting genomic material into discrete partitions such that each discrete partition contains a first individual nucleic acid molecule; (c) providing a population within at least some of the discrete partitions that is enriched for sequences of the fragments comprising at least a portion of the one or more selected portions of the genome; (d) attaching a common barcode sequence to the fragments within each discrete partition such that each of the fragments is attributable to the discrete partition in which it was contained; (e) separating discrete partitions containing fragments comprising at least a portion of the one or more selected portions of the genome from discrete partitions containing no fragments comprising the one or more selected portions of the genome; (f) obtaining sequence information from the fragments comprising at least a portion of the one or more selected portions of the genome, thereby sequencing one or more targeted portions of the genomic sample while retaining molecular context. As will be appreciated, step (a) of such a method can include more than one individual nucleic acid molecule.

In further embodiments and in accordance with any of the above, prior to obtaining sequence information from the fragments, the discrete partitions are combined and the fragments are pooled together. In further embodiments, the step of obtaining sequence information from the fragments is conducted in such a way as to maintain the structural and molecular context of the sequences of the fragments, such that the identifying further comprises identifying fragments derived from nucleic acids located in close physical proximity within the original sample and/or are located on the same first individual nucleic acid molecules. In still further embodiments, this obtaining of sequence information includes a sequencing reaction selected from the group consisting of: short read-length sequencing reactions and long read-length sequencing reactions. In yet further embodiments, the sequencing reaction is a short read, high accuracy sequencing reaction.

In still further embodiments and in accordance with any of the above, the discrete partitions comprise droplets in an emulsion. In further embodiments, the barcoded fragments within the discrete partitions represent about 1×-10× coverage of the one or more selected portions of the genome. In still further embodiments, the barcoded fragments within the discrete partitions represent about 2×-5× coverage of the one or more selected portions of the genome. In yet further embodiments, the barcoded fragments of the amplicons within the discrete partitions represent at least 1× coverage of the one or more selected portions of the genome. In still further embodiments, the barcoded fragments within the discrete partitions represent at least 2× or 5× coverage of the one or more selected portions of the genome.

In addition to providing the ability to obtain sequence information from selected regions of the genome, the methods and systems described herein can also provide other characterizations of genomic material, including without limitation haplotype phasing, identification of structural variations, and identifying copy number variations, as described in detail in U.S. Ser. Nos. 14/316,383; 14/316,398; 14/316,416; 14/316,431; 14/316,447; and 14/316,463 which are herein incorporated by reference in their entirety for all purposes which are herein incorporated by reference in their entirety for all purposes and in particular for all written description, figures and working examples directed to characterization of genomic material.

In one aspect, and in conjunction with any of the methods described above and later herein, the methods and systems described herein provide for the compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned sample nucleic acids, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

The sample nucleic acids utilized in the methods described herein typically represent a number of overlapping portions of the overall sample to be analyzed, e.g., an entire chromosome, exome, or other large genomic portion. These sample nucleic acids may include whole genomes, individual chromosomes, exomes, amplicons, or any of a variety of different nucleic acids of interest. The sample nucleic acids are typically partitioned such that the nucleic acids are present in the partitions in relatively long fragments or stretches of contiguous nucleic acid molecules. Typically, these fragments of the sample nucleic acids may be longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range molecular context described above.

The sample nucleic acids are also typically partitioned at a level whereby a given partition has a very low probability of including two overlapping fragments of the starting sample nucleic acid. This is typically accomplished by providing the sample nucleic acid at a low input amount and/or concentration during the partitioning process. As a result, in preferred cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Published Application No. 2013-0079231 and 2013-0157870) typically only operate with a hundred to a few hundred different barcode sequences, and employ a limiting dilution process of their sample in order to be able to attribute barcodes to different cells/nucleic acids. As such, they will generally operate with far fewer than 100 cells, which would typically provide a ratio of genomes:(barcode type) on the order of 1:10, and certainly well above 1:100. The systems described herein, on the other hand, because of the high level of barcode diversity, e.g., in excess of 10,000, 100,000, 500,000, 600,000, 700,000 etc. diverse barcode types, can operate at genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

Often, the sample is combined with a set of oligonucleotide tags that are releasably-attached to beads prior to the partitioning step. Methods for barcoding nucleic acids are known in the art and described herein. In some examples, methods are utilized as described in Amini et al, 2014, Nature Genetics, Advance Online Publication), which is herein incorporated by reference in its entirety for all purposes and in particular for all teachings related to attaching barcodes or other oligonucleotide tags to nucleic acids. In further examples, the oligonucleotides may comprise at least a first and second region. The first region may be a barcode region that, as between oligonucleotides within a given partition, may be substantially the same barcode sequence, but as between different partitions, may and, in most cases is a different barcode sequence. The second region may be an N-mer (either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, e.g., an exome or other targeted region. As discussed herein, the N-mer may also be designed to selected regions of the genome that tend to be poorly characterized or are highly polymorphic or divergent from the reference sequence. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn, as can analyses across long ranges of genomic sequence—for example, identification of sequence information across stretches of poorly characterized regions of the genome. Such information may also be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Ensemble sample preparation and sequencing methods are predisposed towards primarily identifying and characterizing the majority constituents in the sample, and are not designed to identify and characterize minority constituents, e.g., genetic material contributed by one chromosome, from a poorly characterized or highly polymorphic region of the genome, or material from one or a few cells, or fragmented tumor cell DNA molecule circulating in the bloodstream, that constitute a small percentage of the total DNA in the extracted sample. The methods described herein include selective amplification methods that increase the genetic material from these minority constituents, and the ability to retain the molecular context of this genetic material further provides genetic characterization of these constituents. The described methods and systems also provide a significant advantage for detecting populations that are present within a larger sample. As such, they are particularly useful for assessing haplotype and copy number variations—the methods disclosed herein are also useful for providing sequence information for sequences that were located in spatial proximity to each other within the three dimensional space of the original sample and the original nucleic acid molecules from which those sequences were derived.

The use of the barcoding technique disclosed herein confers the unique capability of providing individual structural and molecular context for sequences and regions of the genome. Such regions of the genome may include a given set of genetic markers, i.e., attributing a given set of genetic markers (as opposed to a single marker) to individual sample nucleic acid molecules, and through variant coordinated assembly, to provide a broader or even longer range inferred individual molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

As noted above, the methods and systems described herein provide individual structural and molecular context for short sequence reads of longer nucleic acids. As used herein, structural context refers to the location of sequences within the three dimensional space of their originating nucleic acid molecules within the original sample. As discussed above, although the genome is often thought of as linear, chromosomes are not rigid, and the spatial distance between two genomic loci does not necessarily correlate to their distance along the genome—genomic regions separated by several megabases along the linear sequence may be immediately proximal to each other in three-dimensional space. By retaining the information of the original spatial proximity of sequence reads, the methods and compositions described herein provide a way to attribute sequence reads to long-range genomic interactions.

Similarly, the retention of individual molecular context possible with the methods described herein provides sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. By providing longer range individual molecular context, the methods and systems of the invention also provide much longer inferred molecular context. Sequence context, as described herein can include lower resolution context, e.g., from mapping the short sequence reads to the individual longer molecules or contigs of linked molecules, as well as the higher resolution sequence context, e.g., from long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

The methods, compositions, and systems described herein allow for characterization of long-range interactions across the genome as well as characterization of associated proteins and other molecules within a sample. Like the higher-level organization of proteins, the bending and folding of DNA and chromatin create functionally significant structures at a wide variety of scales. At small scales, it is well known that DNA is often wound around proteins such as histones to create a structure known as the nucleosome. These nucleosomes pack into larger 'chromatin fibers', and the packing pattern has been implicated as being affected by cellular processes such as transcription. Functional structures also exist at larger scales: regions separated by many megabases long the linear sequence of the genome can be immediately adjacent in 3-dimensional space. Such long-range interactions between genomic loci may play a role in functional characteristics: for example, gene enhancer, silencer and insulator elements may all function across vast genomic distances and their primary mode of action could involve a direct physical association with target genes, noncoding RNAs and/or regulatory elements. Long-range interactions are not limited to elements located in cis, i.e. along the same chromosome, but can also occur between genomic loci located in trans, i.e. on different chromosomes. The existence of long-range interactions can complicate efforts to understand the pathways that regulate cellular processes, because the interacting regulatory elements could lie at a great genomic distance from a target gene, even on another chromosome. In the case of oncogenes and other disease-associated genes, identification of long-range genetic regulators can be of great use in identifying the genomic variants responsible for the disease state and the process by which the disease state is brought about. Thus, the ability to retain structural and molecular context in accordance with the methods described herein provides a way to identify long-range genomic interactions and characterize any associated proteins as well.

The methods described herein are particularly useful for characterization of nucleic acids from an FFPE tissue sample, including a historic FFPE tissue sample. FFPE samples generally present challenges to nucleic acid characterization, because the nucleic acids are often fragmented or otherwise degraded, which can limit the amount of information that can be obtained using conventional methods. The structural and molecular context information that is retained in the methods described herein provides a unique opportunity with such samples, because that contextual information can provide characterizations of long range genomic interactions even for degraded samples, because that long-range information is accessible through short read sequencing technologies. Applications of FFPE nucleic acid characterizations include comparisons of sequences from one or more historic samples to sequences from a sample from a subject, e.g., a cancer patient to provide diagnostic or prognostic information. For example, the status of one or more molecular markers in a historic sample can be correlated with one or more treatment outcomes, and the correlation of a treatment outcome with molecular marker status in one or more historic samples can be used to predict treatment outcomes for the subject, e.g., a cancer patient. These predictions can be the basis for determining whether or not to recommend a drug treatment option to the subject.

V. SAMPLES

As will be appreciated, the methods and systems discussed herein can be used to obtain sequence information from any type of genomic material. Such genomic material may be obtained from a sample taken from a patient. Exemplary samples and types of genomic material of use in the methods and systems discussed herein include without limitation polynucleotides, nucleic acids, oligonucleotides, circulating cell-free nucleic acid, circulating tumor cell (CTC), nucleic acid fragments, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like. In summary, the samples that are used may vary depending on the particular processing needs.

In particular aspects, samples of use in the present invention include formalin fixed paraffin embedded (FFPE) cell and tissue samples and the like, including any other sample types where the risk of sample degradation is high. Other types of fixed samples include without limitation samples that were fixed using: acrolein, glyoxal, osmium tetroxide, carbodiimide, mercuric chloride, zinc salts, picric acid, potassium dichromate, ethanol, methanol, acetone, and/or acetic acid.

In further embodiments, the samples of use in the methods and systems described herein comprise nuclear matrix. "Nuclear matrix" refers to any composition comprising nucleic acids and protein. The nucleic acids may be organized into chromosomes, wherein the proteins (i.e., for example, histones) may become associated with the chromosomes having a regulatory function.

The methods and systems provided herein are particularly useful for nucleic acid sequencing applications in which the starting nucleic acids (e.g., DNA, mRNA, etc.)—or starting target nucleic acids—are present in small quantities, or where nucleic acids that are targeted for analysis, are present at a relatively low proportion of the total nucleic acids within a sample. In one aspect, the present disclosure provides a method of analyzing nucleic acids where the input nucleic acid molecules are present at an amount of less than 50 nanograms (ng). In further embodiments, the nucleic acid molecules are at an input amount of less than less than 40 ng. In some embodiments, the amount is less than 20 ng. In some embodiments, the amount is less than 10 ng. In some embodiments, the amount is less than 5 ng. In some embodiments, the amount is less than 1 ng. In some embodiments, the amount is less than 0.1 ng. Methods for isolating and analyzing nucleic acids where the starting input amount is a small quantity are further described for example in U.S. Ser. No. 14/752,602, filed on Jun. 26, 2015, which is hereby incorporated by reference in its entirety for all purposes and in particular for all teachings related to isolation and characterization of nucleic acids derived from samples in which the nucleic acids are present in small quantities.

As will be appreciated, samples can be processed using methods known in the art at any point during the methods described herein. For example, samples can be processed prior to partitioning or after the sample has been partitioned into discrete partitions.

In certain embodiments, the samples are processed to ensure that longer nucleic acid strands are retained. In embodiments in which FFPE samples are used, such samples may be subjected to processing to remove formaldehyde adducts to improve nucleic acid yields. Such processing methods may include in one non-limiting example the use of water-soluble organocatalysts to speed the reversal of formaldehyde adducts from RNA and DNA bases, as described in Karmakar et al., (2015), Nature Chemistry, DOI: 10.1038/NCHEM.2307, which is hereby incorporated by reference in its entirety and in particular for all teachings related to treatment and processing of FFPE samples.

Any substance that comprises nucleic acid may be the source of a sample. The substance may be a fluid, e.g., a biological fluid. A fluidic substance may include, but not limited to, blood, cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. The substance may be solid, for example, a biological tissue. The substance may comprise normal healthy tissues, diseased tissues, or a mix of healthy and diseased tissues. In some cases, the substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The substance may be associated with various types of organs. Non-limiting examples of organs may include brain, liver, lung, kidney, prostate, ovary, spleen, lymph node (including tonsil), thyroid, pancreas, heart, skeletal muscle, intestine, larynx, esophagus, stomach, or combinations thereof. In some cases, the substance may comprise a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, the substance may comprise contents of a cell, such as, for example, the contents of a single cell or the contents of multiple cells. Methods and systems for analyzing individual cells are provided in, e.g., U.S. Ser. No. 14/752,641, filed Jun. 26, 2015, the full disclosure of which is hereby incorporated by reference in its entirety.

Samples may be obtained from various subjects. A subject may be a living subject or a dead subject. Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. In some case, the subject may be a normal healthy pregnant woman. In some cases, the subject may be a pregnant woman who is at a risking of carrying a baby with certain birth defect.

A sample may be obtained from a subject by any means known in the art. For example, a sample may be obtained from a subject through accessing the circulatory system (e.g., intravenously or intra-arterially via a syringe or other apparatus), collecting a secreted biological sample (e.g., saliva, sputum urine, feces, etc.), surgically (e.g., biopsy) acquiring a biological sample (e.g., intra-operative samples, post-surgical samples, etc.), swabbing (e.g., buccal swab, oropharyngeal swab), or pipetting.

VI. EMBODIMENTS

In some aspects, the present disclosure provides methods of analyzing nucleic acids while maintaining structural context. Such methods include the steps of: (a) providing a sample containing nucleic acids, where the nucleic acids comprise three dimensional structures; (b) separating portions of the sample into discrete partitions such that portions of the nucleic acid three dimensional structures are also separated into the discrete partitions; (c) obtaining sequence information from the nucleic acids, thereby analyzing nucleic acids while maintaining structural context.

In some embodiments, the sequence information from obtaining step (c) includes identification of nucleic acids that are in spatial proximity to each other.

In any embodiments, the obtaining step (c) provides information on intrachromosomal and/or interchromosomal interactions between genomic loci.

In any embodiments, the obtaining step (c) provides information on chromosome conformations.

In any embodiments, prior to separating step (b), at least some of the three dimensional structures are processed to link different portions of the nucleic acids that are in proximity to each other within the three dimensional structures.

In any embodiments, the sample is a formalin-fixed paraffin sample.

In any embodiments, the nucleic acids are not isolated from the sample prior to the separating step (b).

In any embodiments, the discrete partitions comprise beads.

In any embodiments, the beads are gel beads.

In any embodiments, prior to the obtaining step (c), the nucleic acids within the discrete partitions are barcoded to form a plurality of barcoded fragments, where fragments within a given discrete partition each comprise a common barcode, such that the barcodes identify nucleic acids from a given partition.

In any embodiments, the obtaining step (c) comprises a sequencing reaction selected from the group consisting of: short read-length sequencing reactions and long read-length sequencing reactions.

In any embodiments, the sample comprises a tumor sample.

In any embodiments, the sample comprises a mixture of tumor and normal cells.

In any embodiments, the sample comprises a nuclear matrix.

In any embodiments, the nucleic acids comprise RNA.

In any embodiments, the amount of nucleic acids in the sample is less than 5, 10, 15, 20, 25, 30, 35, 40, 45, or 50 ng/ml.

In some aspects, the present disclosure provides methods of analyzing nucleic acids while maintaining structural context that include the steps of (a) forming linked nucleic acids within the sample such that spatially adjacent nucleic acid segments are linked; (b) processing the linked nucleic acids to produce a plurality of ligation products, wherein the ligation products contain portions of the spatially adjacent nucleic acid segments; (c) depositing the plurality of ligation products into discrete partitions; (d) barcoding the ligation products within the discrete partitions to form a plurality of barcoded fragments, wherein fragments within a given discrete partition each comprise a common barcode, thereby associating each fragment with the linked nucleic acid from which it is derived; (e) obtaining sequence information from the plurality of barcoded fragments, thereby analyzing nucleic acids from the sample while maintaining structural context.

In further embodiments, the processing step (b) includes blunt-end ligation under conditions favoring intramolecular ligation, such that the spatially adjacent nucleic acid segments are ligated within the same molecule.

In any embodiments, the conditions favoring intramolecular ligation comprise diluting the sample to reduce concentration of the nucleic acids under 10 ng/pL.

In any embodiments, the nucleic acids are not isolated from the sample prior to the step (a).

In any embodiments, prior to step forming (a), the nucleic acids are immunoprecipitated such that associated DNA binding proteins remain bound to the nucleic acids.

In any embodiments, the partitions comprise beads.

In any embodiments, the beads are gel beads.

In any embodiments, the sample comprises a tumor sample.

In any embodiments, the sample comprises a mixture of tumor and normal cells.

In any embodiments, the processing step includes reversal of the linking subsequent to forming the ligation products.

In any embodiments, the obtaining step (e) provides information on intrachromosomal and/or interchromosomal interactions between genomic loci.

In any embodiments, the obtaining step (e) provides information on chromosome conformations.

In any embodiments, the chromosome conformations are associated with disease states.

In any embodiments, the processing step results in ligation products comprising nucleic acids that were originally in close spatial proximity in the sample.

In any embodiments, the obtaining step (e) comprises a sequencing reaction selected from the group consisting of: short read-length sequencing reactions and long read-length sequencing reactions.

In any embodiments, the sequencing reaction is a short read, high accuracy sequencing reaction.

In any embodiments, the forming step (a) includes cross-linking nucleic acids in the sample.

In any embodiments, the forming step (a) results in covalent links between spatially adjacent nucleic acid segments.

In some aspects, the present disclosure provides methods of analyzing nucleic acids while maintaining structural context that include the steps of: (a) forming linked nucleic acids within the sample such that spatially adjacent nucleic acid segments are linked; (b) depositing the linked nucleic acids into discrete partitions; (c) processing the linked nucleic acids to produce a plurality of ligation products, wherein the ligation products contain portions of the spatially adjacent nucleic acid segments; (d) barcoding the ligation products within the discrete partitions to form a plurality of barcoded fragments, wherein fragments within a given discrete partition each comprise a common barcode, thereby associating each fragment with the linked nucleic acid from which it is derived; (e) obtaining sequence information from the plurality of barcoded fragments, thereby analyzing nucleic acids from the sample while maintaining structural context.

In further embodiments, the processing step (c) includes blunt-end ligation under conditions favoring intramolecular ligation, such that the spatially adjacent nucleic acid segments are ligated within the same molecule.

In any embodiments, the sample is a formalin-fixed paraffin sample.

In any embodiments, the sample comprises a nuclear matrix.

In any embodiments, the nucleic acids comprise RNA.

In any embodiments, the nucleic acids are not isolated from the sample prior to step (a).

In any embodiments, prior to the forming step (a), the nucleic acids are immunoprecipitated such that associated DNA binding proteins remain bound to the nucleic acids.

In any embodiments, the partitions comprise beads.

In any embodiments, the beads are gel beads.

In any embodiments, the sample comprises a tumor sample.

In any embodiments, the sample comprises a mixture of tumor and normal cells.

In any embodiments, the processing step (c) results in ligation products comprising nucleic acids that were originally in close spatial proximity in the sample.

In any embodiments, the obtaining step (e) provides information on intrachromosomal and/or interchromosomal interactions between genomic loci.

In any embodiments, the obtaining step (e) comprises a sequencing reaction selected from the group consisting of: short read-length sequencing reactions and long read-length sequencing reactions.

In any embodiments, the sequencing reaction is a short read, high accuracy sequencing reaction.

In some aspects, the present disclosure provides methods of analyzing nucleic acids while maintaining structural context that include the steps of (a) cross-linking nucleic acids within the sample to form cross-linked nucleic acids, wherein the cross-linking forms covalent links between spatially adjacent nucleic acid segments; (b) depositing the cross-linked nucleic acids into discrete partitions; (c) processing the cross-linked nucleic acids to produce a plurality of ligation products, wherein the ligation products contain portions of the spatially adjacent nucleic acid segments; (d) obtaining sequence information from the plurality of ligation products, thereby analyzing nucleic acids from the sample while maintaining structural context.

In further embodiments the processing step (b) includes blunt-end ligation under conditions favoring intramolecular ligation, such that the spatially adjacent nucleic acid segments are ligated within the same molecule.

In any embodiments, the sample is a formalin-fixed paraffin sample.

In any embodiments, the sample comprises a nuclear matrix.

In any embodiments, the nucleic acids comprise RNA.

In any embodiments, the nucleic acids are not isolated from the sample prior to the cross-linking step (a).

In any embodiments, the amount of nucleic acids in the sample is less than 5, 10, 15, 20, 25, 30, 35, 40, 45, or 50 ng/ml.

In any embodiments, prior to the cross-linking step (a), the nucleic acids are immunoprecipitated such that associated DNA binding proteins remain bound to the nucleic acids.

In any embodiments, prior to the obtaining step (d), the ligation products are associated with a barcode.

In any embodiments, ligation products within the same partition receive common barcodes, such that the barcodes identify ligation products from a given partition.

In any embodiments, the obtaining step (d) comprises a sequencing reaction selected from the group consisting of: short read-length sequencing reactions and long read-length sequencing reactions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Sample Preparation

Figure 7:
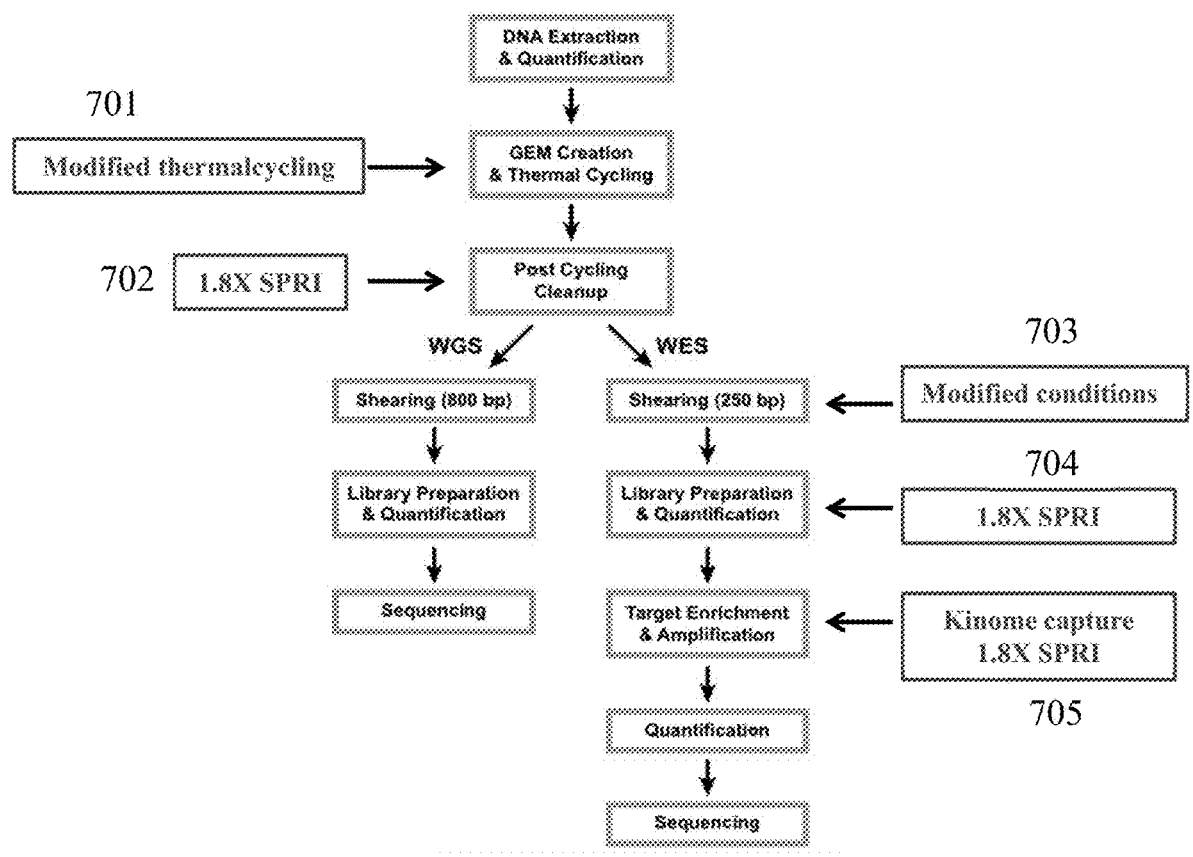
FIG. 7 provides a schematic illustration of an exemplary sample preparation method.

Sample preparation methods were modified to provide long DNA molecules from FFPE samples. FIG. 7 illustrates an exemplary workflow, with modifications indicated for preparing FFPE samples for both whole genome sequencing (WGS) and whole exome sequencing (WES). For example, after DNA extraction, a standard thermalcycling protocol was modified at 701 to move the 98 degree denaturation step from the end of each cycle to the beginning. In addition, a 70 degree hold was added for 2 minutes at the end of each cycle.

During the post cycling cleanup 702 and the WES library preparation and target enrichments steps 704 and 705, 1.8X Solid Phase Reversible Immobilisation (SPRI) beads over normal protocols were used.

Another modification included changing conditions during the shearing step 703, in which an ultrasonicator with a peak incident power of about 450 was used, as opposed to a standard sonicator with a peak incident power of 50.

An additional modification that may be used in certain situations is to first process the FFPE sample with organocatalysts in order to remove formaldehyde adducts, as for example described in Karmakar et al., (2015), Nature Chemistry, DOI: 10.1038/NCHEM.2307. Such protocols include adding 5 mM organocatalysts in 30 mM pH 7 Tris buffer to the samples to effect adduct reversal. Effective organocatalysts include without limitation water-soluble bifunctional catalysts, such as the anthranilate and phosphanilate catalysts described in Karmakar et al. Reversal of the adducts has the effect of improving the yield of nucleic acid yields from the sample.

Example 2

Barcodinq of FFPE Samples

FFPE samples (which can include FFPE samples on a slide) can be tagged with DNA barcodes applied in spatially well-defined pattern, such as those used in DNA microarray printing. The DNA barcode (henceforth called barcode-1) is either long so that it will not diffuse out in subsequent steps or is covalently applied to the FFPE sample. To enable barcoding DNA to get embedded into FFPE slide, the sample is heated, and then the barcodes are added. The barcodes are generally a library of barcodes such that different barcodes are provided in different parts of the slide. The barcodes may also be added in different concentrations in different parts of the slide to assist in the geographic encoding—in that situation, the library of barcodes may comprise identical or different barcodes. After the barcodes are added, the slide is then cooled and then separated into portions generally through cutting in ways such as using laser microdissection, mechanical/acoustic means, and the like. Fluorophores or Qdots may also be used instead of barcodes, however, barcoding enables massively parallel random encapsulation of sample portions while retaining local spatial information (e.g., tumor vs normal cells).

The portions of samples containing the barcodes can then be put in a sequencing system, including a droplet based system such as the 10× Genomics Chromium™ system, such that a single barcoded portion is encapsulated per droplet.

Deparaffinization of the sample can be carried out in the droplet by heating. Paraffin is immiscible in water but soluble in certain oils and thus the paraffin can be easily removed from the droplet upon heating the droplets on-chip. Xylene could also be used in a liquid-liquid extraction process to de-paraffinize the sample portions and ready their nucleic acid contents for further processing.

Further steps include de-cross-linking methylene bridges of the deparaffinized sample. For this step, specialized chemical means can be used to remove the crosslinks and thereby enable access to the contained nucleic acids for any subsequent processing, including the nucleic acid barcoding, amplification, and library preparation steps discussed herein (see for example FIG. 2). Note that the spatial barcoding DNA is also encapsulated in the droplet. The second barcoding step of the individual nucleic acids will serve to barcode the nucleic acids and the barcode used to spatially encode the sample. Sequence reads can then be stitched together to provide information that can then be compared to the original spatial location in the sample and hence related to pathological data.

In alternative versions of this spatial encoding workflow, the de-cross-linking step is first performed within the droplet and then the nucleic acids in the sample, including genomic DNA as well as the spatial encoding barcodes, are attached to particles or are otherwise isolated from the sample. The nucleic acids are then re-encapsulated and subjected to the workflow of barcoding and sequencing in methods described herein, including that pictured in FIG. 2.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method of analyzing nucleic acids from a formalin fixed paraffin embedded (FFPE) sample while maintaining structural context of nucleic acids within the sample, the method comprising:
   (a) forming linked nucleic acids within the FFPE sample such that spatially adjacent nucleic acid segments are linked;
   (b) processing the linked nucleic acids to produce a plurality of ligation products, wherein the ligation products contain portions of the spatially adjacent nucleic acid segments;
   (c) depositing individual portions of the FFPE sample into discrete partitions, wherein each individual portion of the FFPE sample comprises one or more of the ligation products;
   (d) barcoding the ligation products within the discrete partitions to form a plurality of barcoded fragments, wherein fragments within a given discrete partition each comprise a common barcode, thereby associating each fragment with the linked nucleic acid from which it is derived;
   (e) obtaining sequence information from the plurality of barcoded fragments, thereby analyzing nucleic acids from the sample while maintaining structural context.

2. The method of claim 1, wherein the processing step (b) includes blunt-end ligation under conditions favoring intramolecular ligation, such that the spatially adjacent nucleic acid segments are ligated within the same molecule.

3. The method of claim 2, wherein the conditions favoring intramolecular ligation comprise diluting the sample to reduce concentration of the nucleic acids under 10 ng/μL.

4. The method of claim 1, wherein the sample comprises a nuclear matrix.

5. The method of claim 1, wherein the nucleic acids comprise RNA.

6. The method of claim 1, wherein the amount of nucleic acids in the sample is less than 50 ng/ml.

7. The method of claim 1, wherein the partitions comprise beads.

8. The method of claim 7, wherein the beads are gel beads.

9. The method of claim 1, wherein the sample comprises a tumor sample.

10. The method of claim 1, wherein the sample comprises a mixture of tumor and normal cells.

11. The method of claim 1, wherein the processing step includes reversal of the linking subsequent to forming the ligation products.

12. The method of claim 1, wherein the obtaining step (e) provides information on intrachromosomal and/or interchromosomal interactions between genomic loci.

13. The method of claim 1, wherein the obtaining step (e) provides information on chromosome conformations.

14. The method of claim 13, wherein the chromosome conformations are associated with disease states.

15. The method of claim 1, wherein the processing step results in ligation products comprising nucleic acids that were originally in close spatial proximity in the sample.

16. The method of claim 1, wherein the obtaining step (e) comprises a sequencing reaction selected from the group consisting of: short read-length sequencing reactions and long read-length sequencing reactions.

17. The method of claim 16, wherein the sequencing reaction is a short read, high accuracy sequencing reaction.

18. The method of claim 1, wherein the forming step (a) comprises cross-linking nucleic acids in the sample.

19. The method of claim 1, wherein the forming step (a) results in covalent links between spatially adjacent nucleic acid segments.

20. A method of analyzing nucleic acids from a formalin fixed paraffin embedded (FFPE) sample while maintaining structural context of nucleic acids within the sample, the method comprising:
   (a) forming linked nucleic acids within the FFPE sample such that spatially adjacent nucleic acid segments are linked;

(b) depositing individual portions of the FFPE sample into discrete partitions, wherein each individual portion of the FFPE sample comprises one or more linked nucleic acids;

(c) processing the linked nucleic acids to produce a plurality of ligation products, wherein the ligation products contain portions of the spatially adjacent nucleic acid segments;

(d) barcoding the ligation products within the discrete partitions to form a plurality of barcoded fragments, wherein fragments within a given discrete partition each comprise a common barcode, thereby associating each fragment with the linked nucleic acid from which it is derived;

(e) obtaining sequence information from the plurality of barcoded fragments, thereby analyzing nucleic acids from the sample while maintaining structural context.

21. The method of claim 20, wherein the processing step (c) includes blunt-end ligation under conditions favoring intramolecular ligation, such that the spatially adjacent nucleic acid segments are ligated within the same molecule.

22. The method of claim 20, wherein the sample comprises a nuclear matrix.

23. The method of claim 20, wherein the nucleic acids comprise RNA.

24. The method of claim 20, wherein the partitions comprise beads.

25. The method of claim 24, wherein the beads are gel beads.

26. The method of claim 20, wherein the sample comprises a tumor sample.

27. The method of claim 20, wherein the sample comprises a mixture of tumor and normal cells.

28. The method of claim 20, wherein the processing step (c) results in ligation products comprising nucleic acids that were originally in close spatial proximity in the sample.

29. The method of claim 20, wherein the obtaining step (e) provides information on intrachromosomal and/or interchromosomal interactions between genomic loci.

30. The method of claim 20, wherein the obtaining step (e) comprises a sequencing reaction selected from the group consisting of: short read-length sequencing reactions and long read-length sequencing reactions.

31. The method of claim 30, wherein the sequencing reaction is a short read, high accuracy sequencing reaction.

\* \* \* \* \*